US005691308A

United States Patent [19]

Payne et al.

[11] Patent Number: 5,691,308

[45] Date of Patent: Nov. 25, 1997

[54] ***BACILLUS THURINGIENSIS* ISOLATE ACTIVE AGAINST LEPIDOPTERAN PESTS**

[75] Inventors: Jewel Payne, San Diego; August J. Sick, Oceanside, both of Calif.

[73] Assignee: Mycogen Corporation, San Diego, Calif.

[21] Appl. No.: 356,034

[22] Filed: Dec. 14, 1994

Related U.S. Application Data

[63] Continuation of Ser. No. 210,110, Mar. 17, 1994, abandoned, which is a continuation of Ser. No. 865,168, Apr. 9, 1992, abandoned, which is a division of Ser. No. 451,261, Dec. 14, 1989, Pat. No. 5,188,960, which is a continuation-in-part of Ser. No. 371,955, Jun. 27, 1989, Pat. No. 5,126,133.

[51] Int. Cl.$^6$ .......................... A61K 38/16; C07K 14/325; C12N 1/21

[52] U.S. Cl. .......................... 514/12; 530/350; 435/252.3

[58] Field of Search .......................... 424/405, 93.96; 435/171.1, 171.3, 252.1, 252.3, 849; 530/350; 514/12

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,695,455 | 9/1987 | Barnes et al. | 424/93 D |
| 5,273,746 | 12/1993 | Payne et al. | 424/93 |

FOREIGN PATENT DOCUMENTS 0295156 12/1988 European Pat. Off. .

OTHER PUBLICATIONS

Schnepf, H. Ernest, and H.R. Whiteley (1951) "Cloning and expression of the *Bacillus thuringiensis* crystal protein gene in *Escherichia coli*" Proc. Natl. Acad. Sci. USA 75(5):2893–2897.

Sanchis et al. (1988) Molecular Microbiology, vol. 2, No. 3, pp. 393–404.

*Primary Examiner*—Robert A. Wax
*Assistant Examiner*—Kawai Lau
*Attorney, Agent, or Firm*—Saliwanchik, Lloyd & Saliwanchik

[57] ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

2 Claims, 1 Drawing Sheet

A. *Bacillus thuringiensis* HD-1
B. *Bacillus thuringiensis* PS81I

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 3528 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IA2

( x i ) SEQUENCE DESCRIPTION: SEQ ID NO:1:

```
ATGAATAATC AGAATCAATG CGTTCCTTAT AACTGTTTGA ATGATCCGAC AATTGAAATA   60
TTAGAAGGAG AAAGAATAGA AACTGGTTAC ACCCCAATAG ATATTTCCTT GTCGCTAACG  120
CAATTTCTGT TGAGTGAATT TGTCCCAGGT GCTGGGTTTG TATTAGGTTT AATTGATTTA  180
ATATGGGGGT TTGTGGGTCC CTCTCAATGG GATGCATTTC TTGTGCAAAT TGAACAGTTA  240
ATTAACCAAA GAATAGAGGA ATTCGCTAGG AACCAAGCAA TTTCTAGATT AGAAGGGCTA  300
AGCAACCTTT ATCAAATTTA CGCAGAAGCT TTTAGAGAGT GGGAAGCAGA TCCTACTAAT  360
CCAGCATTAA CAGAAGAGAT GCGTATTCAG TTCAATGACA TGAACAGTGC TCTTACAACC  420
GCTATTCCTC TTTTTACAGT TCAAAATTAT CAAGTACCTC TTCTATCAGT ATATGTTCAA  480
GCTGCAAATT TACATTTATC GGTTTTGAGA GATGTTTCAG TGTTTGGACA ACGTTGGGGA  540
TTTGATGTAG CAACAATCAA TAGTCGTTAT AATGATTTAA CTAGGCTTAT TGGCACCTAT  600
ACAGATTATG CTGTACGCTG GTATAATACG GGATTAGAAC GTGTATGGGG ACCGGATTCT  660
AGAGATTGGG TAAGGTATAA TCAATTTAGA AGAGAGCTAA CACTAACTGT ATTAGATATC  720
GTTTCTCTGT TCCCGAACTA TGATAGTAGA ACGTATCCAA TTCGAACAGT TTCCCAATTA  780
ACTAGAGAAA TTTATACAAA CCCAGTATTA GAAAATTTTG ATGGTAGTTT TCGTGGAATG  840
```

-continued

```
GCTCAGAGAA TAGAACAGAA TATTAGGCAA CCACATCTTA TGGATCTCCT TAATAGTATA    900
ACCATTTATA CTGATGTGCA TAGAGGCTTT AATTATTGGT CAGGACATCA AATAACAGCT    960
TCTCCTGTCG GTTTTGCGGG GCCAGAATTT ACTTTTCCTA GATATGGAAC CATGGGAAAT   1020
GCTGCTCCAC CCGTACTGAT CTCAACTACT GGTTTGGGGA TTTTTAGAAC ATTATCTTCA   1080
CCTCTTTACA GAAGAATTAT ACTTGGTTCA GGCCCAAATA ATCAGAACCT GTTTGTCCTT   1140
GATGGAACGG AATTTTCTTT TGCCTCCCTA ACAGCCGATT TACCTTCTAC TATATACAGA   1200
CAAAGGGGAA CGGTCGATTC ACTAGATGTA ATACCGCCAC AGGATAATAG TGTGCCAGCA   1260
CGTGCGGGAT TTAGTCATCG ATTAAGTCAT GTTACAATGC TGAGCCAAGC AGCTGGAGCA   1320
GTTTACACCT TGAGAGCTCC AACGTTTTCT TGGCGACATC GTAGTGCTGA ATTCTCTAAC   1380
CTAATTCCTT CATCACAAAT CACACAGATA CCTTTAACAA AGTCTATTAA TCTTGGCTCT   1440
GGGACCTCTG TTGTTAAAGG ACCAGGATTT ACAGGAGGAG ATATTCTTCG AATAACTTCA   1500
CCTGGCCAGA TTTCAACCTT AAGAGTGACT ATTACGGCAC CATTATCACA AAGATATCGC   1560
GTAAGAATTC GCTACGCTTC TACTACAAAT TTACAATTCC ATACATCAAT TGACGGAAGA   1620
CCTATTAATC AGGGGAATTT TTCAGCAACT ATGAGTAGTG GGGGTAATTT ACAGTCCGGA   1680
AGCTTTAGGA CTGCAGGTTT TACTACTCCG TTTAACTTTT CAAATGGATC AAGTATATTT   1740
ACGTTAAGTG CTCATGTCTT CAATTCAGGC AATGAAGTTT ATATAGAGCG AATTGAATTT   1800
GTTCCGGCAG AAGTAACATT TGAGGCGGAA TATGATTTAG AAAGAGCGCA AGAGGCGGTG   1860
AATGCTCTGT TTACTTCTTC CAATCAACTA GGATTAAAAA CAAATGTGAC GGACTATCAT   1920
ATTGATCAAG TGTCCAATCT AGTCGAATGT TTATCCGGTG AATTCTGTCT GGATGAAAAG   1980
AGAGAATTGT CCGAGAAAGT CAAACATGCG AACCGACTCA GTGATGAGCG GAATTTACTT   2040
CAAGACCCAA ACTTCAGAGG CATCAATAGA CAACCAGACC GTGGCTGGAG AGGCAGTACG   2100
GATATTACCA TCCAAGGAGG AGATGACGTA TTCAAAGAGA ATTACGTCAC ACTACCGGGT   2160
ACCTTTAATG AGTGTTATCC TACGTATCTG TATCAAAAAA TAGATGAGTC GAAATTAAAA   2220
GCCTATACCC GTTACCAATT AAGAGGGTAC ATCGAGGATA GTCAACACTT AGAAATCTAT   2280
TTAATTCGCT ACAATACAAA ACACGAAACA GTAAATGTGC CAGGTACGGG TTCCTTATGG   2340
CCGCTTTCAG TCGAAAATCC AATTGGAAAG TGCGGAGAAC CAAATCGATG CGCACCACAA   2400
CTTGAATGGA ATCCTGATCT AGATTGTTCC TGCAGAGACG GGGAAAAATG TGCACATCAC   2460
TCCCATCATT TCTCCTTGGA CATTGATATT GGATGTACAG ATTTAAATGA GAACTTAGGT   2520
GTATGGGTGA TATTCAAAAT TAAGATGCAA GATGGTCACG CAAGACTAGG TAATCTAGAG   2580
TTTCTCGAAG AGAAACCATT AGTAGGCGAA TCGTTAGCAC GCGTGAAGAG AGCGGAGAAG   2640
AAGTGGAGAG ACAAACGAGA GAAATTGCAA GTGGAAACAA ATATCGTTTA TAAAGAGGCA   2700
AAAGAATCTG TAGATGCTTT ATTTGTGAAC TCTCAATATG ATAGATTACA AGCGGATACC   2760
GACATCGCGA TGATTCATGC GGCAGATAAA CGCGTTCATC GAATTCGAGA AGCATATCTT   2820
CCAGAGTTAT CTGTAATTCC GGGTGTCAAT GCGGGCATTT TTGAAGAATT AGAGGGACGT   2880
ATTTTCACAG CCTACTCTTT ATATGATGCG AGAAATGTCA TTAAAAATGG CGATTTCAAT   2940
AATGGCTTAT CATGCTGGAA CGTGAAAGGG CATGTAGATG TAGAAGAACA AAACAACCAC   3000
CGTTCGGTTC TTGTTGTCCC GGAATGGGAA GCAGAGGTGT CACAAGAGGT TCGTGTCTGT   3060
CCAGGTCGTG GCTATATCCT ACGTGTTACA GCGTACAAAG AGGGATATGG AGAAGGTTGC   3120
GTAACGATTC ATGAGATCGA AGACAATACA GACGAACTGA AATTCAGCAA CTGTGTAGAA   3180
GAGGAAGTAT ATCCAAACAA CACGGTAACG TGTAATGATT ATACTGCAAA TCAAGAAGAA   3240
```

-continued

TACGGGGGTG CGTACACTTC TCGTAATCGT GGATATGGTG AATCTTATGA AAGTAATTCT 3300

TCCATACCAG CTGAGTATGC GCCAGTTTAT GAGGAAGCAT ATATAGATGG AAGAAAAGAG 3360

AATCCTTGTG AATCTAACAG AGGATATGGG GATTACACGC CACTACCAGC TGGTTATGTG 3420

ACAAAAGAAT TAGAGTACTT CCCAGAAACC GATAAGGTAT GGATTGAGAT CGGGGAAACG 3480

GAAGGAACAT TCATCGTGGA TAGCGTGGAA TTACTCCTTA TGGAGGAA 3528

( 2 ) INFORMATION FOR SEQ ID NO:2:

( i ) SEQUENCE CHARACTERISTICS:
( A ) LENGTH: 1176 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IA2

( x i ) SEQUENCE DESCRIPTION: SEQ ID NO:2:

Met Asn Asn Gln Asn Gln Cys Val Pro Tyr Asn Cys Leu Asn Asp Pro
1 5 10 15

Thr Ile Glu Ile Leu Glu Gly Glu Arg Ile Glu Thr Gly Tyr Thr Pro
20 25 30

Ile Asp Ile Ser Leu Ser Leu Thr Gln Phe Leu Leu Ser Glu Phe Val
35 40 45

Pro Gly Ala Gly Phe Val Leu Gly Leu Ile Asp Leu Ile Trp Gly Phe
50 55 60

Val Gly Pro Ser Gln Trp Asp Ala Phe Leu Val Gln Ile Glu Gln Leu
65 70 75 80

Ile Asn Gln Arg Ile Glu Glu Phe Ala Arg Asn Gln Ala Ile Ser Arg
85 90 95

Leu Glu Gly Leu Ser Asn Leu Tyr Gln Ile Tyr Ala Glu Ala Phe Arg
100 105 110

Glu Trp Glu Ala Asp Pro Thr Asn Pro Ala Leu Thr Glu Glu Met Arg
115 120 125

Ile Gln Phe Asn Asp Met Asn Ser Ala Leu Thr Thr Ala Ile Pro Leu
130 135 140

Phe Thr Val Gln Asn Tyr Gln Val Pro Leu Leu Ser Val Tyr Val Gln
145 150 155 160

Ala Ala Asn Leu His Leu Ser Val Leu Arg Asp Val Ser Val Phe Gly
165 170 175

Gln Arg Trp Gly Phe Asp Val Ala Thr Ile Asn Ser Arg Tyr Asn Asp
180 185 190

Leu Thr Arg Leu Ile Gly Thr Tyr Thr Asp Tyr Ala Val Arg Trp Tyr
195 200 205

Asn Thr Gly Leu Glu Arg Val Trp Gly Pro Asp Ser Arg Asp Trp Val
210 215 220

Arg Tyr Asn Gln Phe Arg Arg Glu Leu Thr Leu Thr Val Leu Asp Ile

-continued 225 230 235 240

Val Ser Leu Phe Pro Asn Tyr Asp Ser Arg Thr Tyr Pro Ile Arg Thr
245 250 255

Val Ser Gln Leu Thr Arg Glu Ile Tyr Thr Asn Pro Val Leu Glu Asn
260 265 270

Phe Asp Gly Ser Phe Arg Gly Met Ala Gln Arg Ile Glu Gln Asn Ile
275 280 285

Arg Gln Pro His Leu Met Asp Leu Leu Asn Ser Ile Thr Ile Tyr Thr
290 295 300

Asp Val His Arg Gly Phe Asn Tyr Trp Ser Gly His Gln Ile Thr Ala
305 310 315 320

Ser Pro Val Gly Phe Ala Gly Pro Glu Phe Thr Phe Pro Arg Tyr Gly
325 330 335

Thr Met Gly Asn Ala Ala Pro Pro Val Leu Ile Ser Thr Thr Gly Leu
340 345 350

Gly Ile Phe Arg Thr Leu Ser Ser Pro Leu Tyr Arg Arg Ile Ile Leu
355 360 365

Gly Ser Gly Pro Asn Asn Gln Asn Leu Phe Val Leu Asp Gly Thr Glu
370 375 380

Phe Ser Phe Ala Ser Leu Thr Ala Asp Leu Pro Ser Thr Ile Tyr Arg
385 390 395 400

Gln Arg Gly Thr Val Asp Ser Leu Asp Val Ile Pro Pro Gln Asp Asn
405 410 415

Ser Val Pro Ala Arg Ala Gly Phe Ser His Arg Leu Ser His Val Thr
420 425 430

Met Leu Ser Gln Ala Ala Gly Ala Val Tyr Thr Leu Arg Ala Pro Thr
435 440 445

Phe Ser Trp Arg His Arg Ser Ala Glu Phe Ser Asn Leu Ile Pro Ser
450 455 460

Ser Gln Ile Thr Gln Ile Pro Leu Thr Lys Ser Ile Asn Leu Gly Ser
465 470 475 480

Gly Thr Ser Val Val Lys Gly Pro Gly Phe Thr Gly Gly Asp Ile Leu
485 490 495

Arg Ile Thr Ser Pro Gly Gln Ile Ser Thr Leu Arg Val Thr Ile Thr
500 505 510

Ala Pro Leu Ser Gln Arg Tyr Arg Val Arg Ile Arg Tyr Ala Ser Thr
515 520 525

Thr Asn Leu Gln Phe His Thr Ser Ile Asp Gly Arg Pro Ile Asn Gln
530 535 540

Gly Asn Phe Ser Ala Thr Met Ser Ser Gly Gly Asn Leu Gln Ser Gly
545 550 555 560

Ser Phe Arg Thr Ala Gly Phe Thr Thr Pro Phe Asn Phe Ser Asn Gly
565 570 575

Ser Ser Ile Phe Thr Leu Ser Ala His Val Phe Asn Ser Gly Asn Glu
580 585 590

Val Tyr Ile Glu Arg Ile Glu Phe Val Pro Ala Glu Val Thr Phe Glu
595 600 605

Ala Glu Tyr Asp Leu Glu Arg Ala Gln Glu Ala Val Asn Ala Leu Phe
610 615 620

Thr Ser Ser Asn Gln Leu Gly Leu Lys Thr Asn Val Thr Asp Tyr His
625 630 635 640

Ile Asp Gln Val Ser Asn Leu Val Glu Cys Leu Ser Gly Glu Phe Cys
645 650 655

-continued

| | | | | | | | | | | | | | | | |
|---|---|---|---|---|---|---|---|---|---|---|---|---|---|---|---|
| Leu | Asp | Glu | Lys | Arg | Glu | Leu | Ser | Glu | Lys | Val | Lys | His | Ala | Asn | Arg |
| | | | 660 | | | | | 665 | | | | | 670 | | |
| Leu | Ser | Asp | Glu | Arg | Asn | Leu | Leu | Gln | Asp | Pro | Asn | Phe | Arg | Gly | Ile |
| | | 675 | | | | | 680 | | | | | 685 | | | |
| Asn | Arg | Gln | Pro | Asp | Arg | Gly | Trp | Arg | Gly | Ser | Thr | Asp | Ile | Thr | Ile |
| | 690 | | | | | 695 | | | | | 700 | | | | |
| Gln | Gly | Gly | Asp | Asp | Val | Phe | Lys | Glu | Asn | Tyr | Val | Thr | Leu | Pro | Gly |
| 705 | | | | | 710 | | | | | 715 | | | | | 720 |
| Thr | Phe | Asn | Glu | Cys | Tyr | Pro | Thr | Tyr | Leu | Tyr | Gln | Lys | Ile | Asp | Glu |
| | | | | 725 | | | | | 730 | | | | | 735 | |
| Ser | Lys | Leu | Lys | Ala | Tyr | Thr | Arg | Tyr | Gln | Leu | Arg | Gly | Tyr | Ile | Glu |
| | | | 740 | | | | | 745 | | | | | 750 | | |
| Asp | Ser | Gln | His | Leu | Glu | Ile | Tyr | Leu | Ile | Arg | Tyr | Asn | Thr | Lys | His |
| | | 755 | | | | | 760 | | | | | 765 | | | |
| Glu | Thr | Val | Asn | Val | Pro | Gly | Thr | Gly | Ser | Leu | Trp | Pro | Leu | Ser | Val |
| | 770 | | | | | 775 | | | | | 780 | | | | |
| Glu | Asn | Pro | Ile | Gly | Lys | Cys | Gly | Glu | Pro | Asn | Arg | Cys | Ala | Pro | Gln |
| 785 | | | | | 790 | | | | | 795 | | | | | 800 |
| Leu | Glu | Trp | Asn | Pro | Asp | Leu | Asp | Cys | Ser | Cys | Arg | Asp | Gly | Glu | Lys |
| | | | | 805 | | | | | 810 | | | | | 815 | |
| Cys | Ala | His | His | Ser | His | His | Phe | Ser | Leu | Asp | Ile | Asp | Ile | Gly | Cys |
| | | | 820 | | | | | 825 | | | | | 830 | | |
| Thr | Asp | Leu | Asn | Glu | Asn | Leu | Gly | Val | Trp | Val | Ile | Phe | Lys | Ile | Lys |
| | | 835 | | | | | 840 | | | | | 845 | | | |
| Met | Gln | Asp | Gly | His | Ala | Arg | Leu | Gly | Asn | Leu | Glu | Phe | Leu | Glu | Glu |
| | 850 | | | | | 855 | | | | | 860 | | | | |
| Lys | Pro | Leu | Val | Gly | Glu | Ser | Leu | Ala | Arg | Val | Lys | Arg | Ala | Glu | Lys |
| 865 | | | | | 870 | | | | | 875 | | | | | 880 |
| Lys | Trp | Arg | Asp | Lys | Arg | Glu | Lys | Leu | Gln | Val | Glu | Thr | Asn | Ile | Val |
| | | | | 885 | | | | | 890 | | | | | 895 | |
| Tyr | Lys | Glu | Ala | Lys | Glu | Ser | Val | Asp | Ala | Leu | Phe | Val | Asn | Ser | Gln |
| | | | 900 | | | | | 905 | | | | | 910 | | |
| Tyr | Asp | Arg | Leu | Gln | Ala | Asp | Thr | Asp | Ile | Ala | Met | Ile | His | Ala | Ala |
| | | 915 | | | | | 920 | | | | | 925 | | | |
| Asp | Lys | Arg | Val | His | Arg | Ile | Arg | Glu | Ala | Tyr | Leu | Pro | Glu | Leu | Ser |
| | 930 | | | | | 935 | | | | | 940 | | | | |
| Val | Ile | Pro | Gly | Val | Asn | Ala | Gly | Ile | Phe | Glu | Glu | Leu | Glu | Gly | Arg |
| 945 | | | | | 950 | | | | | 955 | | | | | 960 |
| Ile | Phe | Thr | Ala | Tyr | Ser | Leu | Tyr | Asp | Ala | Arg | Asn | Val | Ile | Lys | Asn |
| | | | | 965 | | | | | 970 | | | | | 975 | |
| Gly | Asp | Phe | Asn | Asn | Gly | Leu | Ser | Cys | Trp | Asn | Val | Lys | Gly | His | Val |
| | | | 980 | | | | | 985 | | | | | 990 | | |
| Asp | Val | Glu | Glu | Gln | Asn | Asn | His | Arg | Ser | Val | Leu | Val | Val | Pro | Glu |
| | | 995 | | | | | 1000 | | | | | 1005 | | | |
| Trp | Glu | Ala | Glu | Val | Ser | Gln | Glu | Val | Arg | Val | Cys | Pro | Gly | Arg | Gly |
| | 1010 | | | | | 1015 | | | | | 1020 | | | | |
| Tyr | Ile | Leu | Arg | Val | Thr | Ala | Tyr | Lys | Glu | Gly | Tyr | Gly | Glu | Gly | Cys |
| 1025 | | | | | 1030 | | | | | 1035 | | | | | 1040 |
| Val | Thr | Ile | His | Glu | Ile | Glu | Asp | Asn | Thr | Asp | Glu | Leu | Lys | Phe | Ser |
| | | | | 1045 | | | | | 1050 | | | | | 1055 | |
| Asn | Cys | Val | Glu | Glu | Glu | Val | Tyr | Pro | Asn | Asn | Thr | Val | Thr | Cys | Asn |
| | | | 1060 | | | | | 1065 | | | | | 1070 | | |
| Asp | Tyr | Thr | Ala | Asn | Gln | Glu | Glu | Tyr | Gly | Gly | Ala | Tyr | Thr | Ser | Arg |
| | | 1075 | | | | | 1080 | | | | | 1085 | | | |

-continued

Asn Arg Gly Tyr Gly Glu Ser Tyr Glu Ser Asn Ser Ser Ile Pro Ala
1090 1095 1100

Glu Tyr Ala Pro Val Tyr Glu Glu Ala Tyr Ile Asp Gly Arg Lys Glu
1105 1110 1115 1120

Asn Pro Cys Glu Ser Asn Arg Gly Tyr Gly Asp Tyr Thr Pro Leu Pro
1125 1130 1135

Ala Gly Tyr Val Thr Lys Glu Leu Glu Tyr Phe Pro Glu Thr Asp Lys
1140 1145 1150

Val Trp Ile Glu Ile Gly Glu Thr Glu Gly Thr Phe Ile Val Asp Ser
1155 1160 1165

Val Glu Leu Leu Leu Met Glu Glu
1170 1175

( 2 ) INFORMATION FOR SEQ ID NO:3:

( i ) SEQUENCE CHARACTERISTICS:
( A ) LENGTH: 3495 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IB ( x i ) SEQUENCE DESCRIPTION: SEQ ID NO:3:

ATGGAAATAA ATAATCAAAA CCAATGTGTG CCTTACAATT GTTTAAGTAA TCCTAAGGAG 60

ATAATATTAG GCGAGGAAAG GCTAGAAACA GGGAATACTG TAGCAGACAT TTCATTAGGG 120

CTTATTAATT TTCTATATTC TAATTTTGTA CCAGGAGGAG GATTTATAGT AGGTTTACTA 180

GAATTAATAT GGGGATTTAT AGGGCCTTCG CAATGGGATA TTTTTTTAGC TCAAATTGAG 240

CAATTGATTA GTCAAAGAAT AGAAGAATTT GCTAGGAATC AGGCAATTTC AAGATTGGAG 300

GGGCTAAGCA ATCTTTATAA GGTCTATGTT AGAGCGTTTA GCGACTGGGA GAAAGATCCT 360

ACTAATCCTG CTTTAAGGGA AGAAATGCGT ATACAATTTA ATGACATGAA TAGTGCTCTC 420

ATAACGGCTA TTCCACTTTT TAGAGTTCAA AATTATGAAG TTGCTCTTTT ATCTGTATAT 480

GTTCAAGCCG CAAACTTACA TTTATCTATT TTAAGGGATG TTTCAGTTTT CGGAGAAAGA 540

TGGGGATATG ATACAGCGAC TATCAATAAT CGCTATAGTG ATCTGACTAG CCTTATTCAT 600

GTTTATACTA ACCATTGTGT GGATACGTAT AATCAGGGAT TAAGGCGTTT GGAAGGTCGT 660

TTTCTTAGCG ATTGGATTGT ATATAATCGT TTCCGGAGAC AATTGACAAT TTCAGTATTA 720

GATATTGTTG CGTTTTTTCC AAATTATGAT ATTAGAACAT ATCCAATTCA AACAGCTACT 780

CAGCTAACGA GGGAAGTCTA TCTGGATTTA CCTTTTATTA ATGAAAATCT TTCTCCTGCA 840

GCAAGCTATC CAACCTTTTC AGCTGCTGAA AGTGCTATAA TTAGAAGTCC TCATTTAGTA 900

GACTTTTTAA ATAGCTTTAC CATTTATACA GATAGTCTGG CACGTTATGC ATATTGGGGA 960

GGGCACTTGG TAAATTCTTT CCGCACAGGA ACCACTACTA ATTTGATAAG ATCCCCTTTA 1020

TATGGAAGGG AAGGAAATAC AGAGCGCCCC GTAACTATTA CCGCATCACC TAGCGTACCA 1080

-continued

ATATTTAGAA CACTTTCATA TATTACAGGC CTTGACAATT CAAATCCTGT AGCTGGAATC 1140

GAGGGAGTGG AATTCCAAAA TACTATAAGT AGAAGTATCT ATCGTAAAAG CGGTCCAATA 1200

GATTCTTTTA GTGAATTACC ACCTCAAGAT GCCAGCGTAT CTCCTGCAAT TGGGTATAGT 1260

CACCGTTTAT GCCATGCAAC ATTTTTAGAA CGGATTAGTG GACCAAGAAT AGCAGGCACC 1320

GTATTTTCTT GGACACACCG TAGTGCCAGC CCTACTAATG AAGTAAGTCC ATCTAGAATT 1380

ACACAAATTC CATGGGTAAA GGCGCATACT CTTGCATCTG GTGCCTCCGT CATTAAAGGT 1440

CCTGGATTTA CAGGTGGAGA TATTCTGACT AGGAATAGTA TGGGCGAGCT GGGGACCTTA 1500

CGAGTAACCT TCACAGGAAG ATTACCACAA AGTTATTATA TACGTTTCCG TTATGCTTCG 1560

GTAGCAAATA GGAGTGGTAC ATTTAGATAT TCACAGCCAC CTTCGTATGG AATTTCATTT 1620

CCAAAAACTA TGGACGCAGG TGAACCACTA ACATCTCGTT CGTTCGCTCA TACAACACTC 1680

TTCACTCCAA TAACCTTTTC ACGAGCTCAA GAAGAATTTG ATCTATACAT CCAATCGGGT 1740

GTTTATATAG ATCGAATTGA ATTTATACCG GTTACTGCAA CATTTGAGGC AGAATATGAT 1800

TTAGAAAGAG CGCAAAAGGT GGTGAATGCC CTGTTTACGT CTACAAACCA ACTAGGGCTA 1860

AAAACAGATG TGACGGATTA TCATATTGAT CAGGTATCCA ATCTAGTTGC GTGTTTATCG 1920

GATGAATTTT GTCTGGATGA AAAGAGAGAA TTGTCCGAGA AAGTTAAACA TGCAAAGCGA 1980

CTCAGTGATG AGCGGAATTT ACTTCAAGAT CCAAACTTCA GAGGGATCAA TAGGCAACCA 2040

GACCGTGGCT GGAGAGGAAG TACGGATATT ACTATCCAAG GAGGAGATGA CGTATTCAAA 2100

GAGAATTACG TTACGCTACC GGGTACCTTT GATGAGTGCT ATCCAACGTA TTTATATCAA 2160

AAAATAGATG AGTCGAAATT AAAAGCCTAT ACCCGTTATC AATTAAGAGG GTATATCGAA 2220

GATAGTCAAG ACTTAGAAAT CTATTTAATT CGTTACAATG CAAAACACGA AATAGTAAAT 2280

GTACCAGGTA CAGGAAGTTT ATGGCCTCTT TCTGTAGAAA ATCAAATTGG ACCTTGTGGA 2340

GAACCGAATC GATGCGCGCC ACACCTTGAA TGGAATCCTG ATTTACACTG TTCCTGCAGA 2400

GACGGGGAAA AATGTGCACA TCATTCTCAT CATTTCTCTT TGGACATTGA TGTTGGATGT 2460

ACAGACTTAA ATGAGGACTT AGGTGTATGG GTGATATTCA AGATTAAGAC GCAAGATGGC 2520

CACGCACGAC TAGGGAATCT AGAGTTTCTC GAAGAGAAAC CATTATTAGG AGAAGCACTA 2580

GCTCGTGTGA AAAGAGCGGA GAAAAAATGG AGAGACAAAC GCGAAACATT ACAATTGGAA 2640

ACAACTATCG TTTATAAAGA GGCAAAAGAA TCTGTAGATG CTTTATTTGT AAACTCTCAA 2700

TATGATAGAT TACAAGCGGA TACGAACATC GCGATGATTC ATGCGGCAGA TAAACGCGTT 2760

CATAGAATTC GAGAAGCGTA TCTGCCGGAG CTGTCTGTGA TTCCGGGTGT CAATGCGGCT 2820

ATTTTTGAAG AATTAGAAGA GCGTATTTTC ACTGCATTTT CCCTATATGA TGCGAGAAAT 2880

ATTATTAAAA ATGGCGATTT CAATAATGGC TTATTATGCT GGAACGTGAA AGGGCATGTA 2940

GAGGTAGAAG AACAAAACAA TCACCGTTCA GTCCTGGTTA TCCCAGAATG GGAGGCAGAA 3000

GTGTCACAAG AGGTTCGTGT CTGTCCAGGT CGTGGCTATA TCCTTCGTGT TACAGCGTAC 3060

AAAGAGGGAT ATGGAGAAGG TTGCGTAACG ATCCATGAGA TCGAGAACAA TACAGACGAA 3120

CTGAAATTCA ACAACTGTGT AGAAGAGGAA GTATATCCAA ACAACACGGT AACGTGTATT 3180

AATTATACTG CGACTCAAGA AGAATATGAG GGTACGTACA CTTCTCGTAA TCGAGGATAT 3240

GACGAAGCCT ATGGTAATAA CCCTTCCGTA CCAGCTGATT ATGCGTCAGT CTATGAAGAA 3300

AAATCGTATA CAGATAGACG AAGAGAGAAT CCTTGTGAAT CTAACAGAGG ATATGGAGAT 3360

TACACACCAC TACCAGCTGG TTATGTAACA AAGGAATTAG AGTACTTCCC AGAGACCGAT 3420

AAGGTATGGA TTGAGATTGG AGAAACAGAA GGAACATTCA TCGTGGACAG CGTGGAATTA 3480

-continued

CTCCTTATGG AGGAA 3495

( 2 ) INFORMATION FOR SEQ ID NO:4:

( i ) SEQUENCE CHARACTERISTICS:
( A ) LENGTH: 1165 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IB ( x i ) SEQUENCE DESCRIPTION: SEQ ID NO:4:

Met Glu Ile Asn Asn Gln Asn Gln Cys Val Pro Tyr Asn Cys Leu Ser
1 5 10 15

Asn Pro Lys Glu Ile Ile Leu Gly Glu Glu Arg Leu Glu Thr Gly Asn
20 25 30

Thr Val Ala Asp Ile Ser Leu Gly Leu Ile Asn Phe Leu Tyr Ser Asn
35 40 45

Phe Val Pro Gly Gly Gly Phe Ile Val Gly Leu Leu Glu Leu Ile Trp
50 55 60

Gly Phe Ile Gly Pro Ser Gln Trp Asp Ile Phe Leu Ala Gln Ile Glu
65 70 75 80

Gln Leu Ile Ser Gln Arg Ile Glu Glu Phe Ala Arg Asn Gln Ala Ile
85 90 95

Ser Arg Leu Glu Gly Leu Ser Asn Leu Tyr Lys Val Tyr Val Arg Ala
100 105 110

Phe Ser Asp Trp Glu Lys Asp Pro Thr Asn Pro Ala Leu Arg Glu Glu
115 120 125

Met Arg Ile Gln Phe Asn Asp Met Asn Ser Ala Leu Ile Thr Ala Ile
130 135 140

Pro Leu Phe Arg Val Gln Asn Tyr Glu Val Ala Leu Leu Ser Val Tyr
145 150 155 160

Val Gln Ala Ala Asn Leu His Leu Ser Ile Leu Arg Asp Val Ser Val
165 170 175

Phe Gly Glu Arg Trp Gly Tyr Asp Thr Ala Thr Ile Asn Asn Arg Tyr
180 185 190

Ser Asp Leu Thr Ser Leu Ile His Val Tyr Thr Asn His Cys Val Asp
195 200 205

Thr Tyr Asn Gln Gly Leu Arg Arg Leu Glu Gly Arg Phe Leu Ser Asp
210 215 220

Trp Ile Val Tyr Asn Arg Phe Arg Arg Gln Leu Thr Ile Ser Val Leu
225 230 235 240

Asp Ile Val Ala Phe Phe Pro Asn Tyr Asp Ile Arg Thr Tyr Pro Ile
245 250 255

Gln Thr Ala Thr Gln Leu Thr Arg Glu Val Tyr Leu Asp Leu Pro Phe
260 265 270

-continued

| | | | | | | | | | | | | | | | |
|---|---|---|---|---|---|---|---|---|---|---|---|---|---|---|---|
| Ile | Asn | Glu | Asn | Leu | Ser | Pro | Ala | Ala | Ser | Tyr | Pro | Thr | Phe | Ser | Ala |
| | | 275 | | | | | 280 | | | | | 285 | | | |
| Ala | Glu | Ser | Ala | Ile | Ile | Arg | Ser | Pro | His | Leu | Val | Asp | Phe | Leu | Asn |
| | 290 | | | | | 295 | | | | | 300 | | | | |
| Ser | Phe | Thr | Ile | Tyr | Thr | Asp | Ser | Leu | Ala | Arg | Tyr | Ala | Tyr | Trp | Gly |
| 305 | | | | | 310 | | | | | 315 | | | | | 320 |
| Gly | His | Leu | Val | Asn | Ser | Phe | Arg | Thr | Gly | Thr | Thr | Thr | Asn | Leu | Ile |
| | | | | 325 | | | | | 330 | | | | | 335 | |
| Arg | Ser | Pro | Leu | Tyr | Gly | Arg | Glu | Gly | Asn | Thr | Glu | Arg | Pro | Val | Thr |
| | | | 340 | | | | | 345 | | | | | 350 | | |
| Ile | Thr | Ala | Ser | Pro | Ser | Val | Pro | Ile | Phe | Arg | Thr | Leu | Ser | Tyr | Ile |
| | | 355 | | | | | 360 | | | | | 365 | | | |
| Thr | Gly | Leu | Asp | Asn | Ser | Asn | Pro | Val | Ala | Gly | Ile | Glu | Gly | Val | Glu |
| | 370 | | | | | 375 | | | | | 380 | | | | |
| Phe | Gln | Asn | Thr | Ile | Ser | Arg | Ser | Ile | Tyr | Arg | Lys | Ser | Gly | Pro | Ile |
| 385 | | | | | 390 | | | | | 395 | | | | | 400 |
| Asp | Ser | Phe | Ser | Glu | Leu | Pro | Pro | Gln | Asp | Ala | Ser | Val | Ser | Pro | Ala |
| | | | | 405 | | | | | 410 | | | | | 415 | |
| Ile | Gly | Tyr | Ser | His | Arg | Leu | Cys | His | Ala | Thr | Phe | Leu | Glu | Arg | Ile |
| | | | 420 | | | | | 425 | | | | | 430 | | |
| Ser | Gly | Pro | Arg | Ile | Ala | Gly | Thr | Val | Phe | Ser | Trp | Thr | His | Arg | Ser |
| | | 435 | | | | | 440 | | | | | 445 | | | |
| Ala | Ser | Pro | Thr | Asn | Glu | Val | Ser | Pro | Ser | Arg | Ile | Thr | Gln | Ile | Pro |
| | 450 | | | | | 455 | | | | | 460 | | | | |
| Trp | Val | Lys | Ala | His | Thr | Leu | Ala | Ser | Gly | Ala | Ser | Val | Ile | Lys | Gly |
| 465 | | | | | 470 | | | | | 475 | | | | | 480 |
| Pro | Gly | Phe | Thr | Gly | Gly | Asp | Ile | Leu | Thr | Arg | Asn | Ser | Met | Gly | Glu |
| | | | | 485 | | | | | 490 | | | | | 495 | |
| Leu | Gly | Thr | Leu | Arg | Val | Thr | Phe | Thr | Gly | Arg | Leu | Pro | Gln | Ser | Tyr |
| | | | 500 | | | | | 505 | | | | | 510 | | |
| Tyr | Ile | Arg | Phe | Arg | Tyr | Ala | Ser | Val | Ala | Asn | Arg | Ser | Gly | Thr | Phe |
| | | 515 | | | | | 520 | | | | | 525 | | | |
| Arg | Tyr | Ser | Gln | Pro | Pro | Ser | Tyr | Gly | Ile | Ser | Phe | Pro | Lys | Thr | Met |
| | 530 | | | | | 535 | | | | | 540 | | | | |
| Asp | Ala | Gly | Glu | Pro | Leu | Thr | Ser | Arg | Ser | Phe | Ala | His | Thr | Thr | Leu |
| 545 | | | | | 550 | | | | | 555 | | | | | 560 |
| Phe | Thr | Pro | Ile | Thr | Phe | Ser | Arg | Ala | Gln | Glu | Glu | Phe | Asp | Leu | Tyr |
| | | | | 565 | | | | | 570 | | | | | 575 | |
| Ile | Gln | Ser | Gly | Val | Tyr | Ile | Asp | Arg | Ile | Glu | Phe | Ile | Pro | Val | Thr |
| | | | 580 | | | | | 585 | | | | | 590 | | |
| Ala | Thr | Phe | Glu | Ala | Glu | Tyr | Asp | Leu | Glu | Arg | Ala | Gln | Lys | Val | Val |
| | | 595 | | | | | 600 | | | | | 605 | | | |
| Asn | Ala | Leu | Phe | Thr | Ser | Thr | Asn | Gln | Leu | Gly | Leu | Lys | Thr | Asp | Val |
| | 610 | | | | | 615 | | | | | 620 | | | | |
| Thr | Asp | Tyr | His | Ile | Asp | Gln | Val | Ser | Asn | Leu | Val | Ala | Cys | Leu | Ser |
| 625 | | | | | 630 | | | | | 635 | | | | | 640 |
| Asp | Glu | Phe | Cys | Leu | Asp | Glu | Lys | Arg | Glu | Leu | Ser | Glu | Lys | Val | Lys |
| | | | | 645 | | | | | 650 | | | | | 655 | |
| His | Ala | Lys | Arg | Leu | Ser | Asp | Glu | Arg | Asn | Leu | Leu | Gln | Asp | Pro | Asn |
| | | | 660 | | | | | 665 | | | | | 670 | | |
| Phe | Arg | Gly | Ile | Asn | Arg | Gln | Pro | Asp | Arg | Gly | Trp | Arg | Gly | Ser | Thr |
| | | 675 | | | | | 680 | | | | | 685 | | | |
| Asp | Ile | Thr | Ile | Gln | Gly | Gly | Asp | Asp | Val | Phe | Lys | Glu | Asn | Tyr | Val |
| | 690 | | | | | 695 | | | | | 700 | | | | |

-continued

Thr Leu Pro Gly Thr Phe Asp Glu Cys Tyr Pro Thr Tyr Leu Tyr Gln
705 710 715 720

Lys Ile Asp Glu Ser Lys Leu Lys Ala Tyr Thr Arg Tyr Gln Leu Arg
725 730 735

Gly Tyr Ile Glu Asp Ser Gln Asp Leu Glu Ile Tyr Leu Ile Arg Tyr
740 745 750

Asn Ala Lys His Glu Ile Val Asn Val Pro Gly Thr Gly Ser Leu Trp
755 760 765

Pro Leu Ser Val Glu Asn Gln Ile Gly Pro Cys Gly Glu Pro Asn Arg
770 775 780

Cys Ala Pro His Leu Glu Trp Asn Pro Asp Leu His Cys Ser Cys Arg
785 790 795 800

Asp Gly Glu Lys Cys Ala His His Ser His His Phe Ser Leu Asp Ile
805 810 815

Asp Val Gly Cys Thr Asp Leu Asn Glu Asp Leu Gly Val Trp Val Ile
820 825 830

Phe Lys Ile Lys Thr Gln Asp Gly His Ala Arg Leu Gly Asn Leu Glu
835 840 845

Phe Leu Glu Glu Lys Pro Leu Leu Gly Glu Ala Leu Ala Arg Val Lys
850 855 860

Arg Ala Glu Lys Lys Trp Arg Asp Lys Arg Glu Thr Leu Gln Leu Glu
865 870 875 880

Thr Thr Ile Val Tyr Lys Glu Ala Lys Glu Ser Val Asp Ala Leu Phe
885 890 895

Val Asn Ser Gln Tyr Asp Arg Leu Gln Ala Asp Thr Asn Ile Ala Met
900 905 910

Ile His Ala Ala Asp Lys Arg Val His Arg Ile Arg Glu Ala Tyr Leu
915 920 925

Pro Glu Leu Ser Val Ile Pro Gly Val Asn Ala Ala Ile Phe Glu Glu
930 935 940

Leu Glu Glu Arg Ile Phe Thr Ala Phe Ser Leu Tyr Asp Ala Arg Asn
945 950 955 960

Ile Ile Lys Asn Gly Asp Phe Asn Asn Gly Leu Leu Cys Trp Asn Val
965 970 975

Lys Gly His Val Glu Val Glu Glu Gln Asn Asn His Arg Ser Val Leu
980 985 990

Val Ile Pro Glu Trp Glu Ala Glu Val Ser Gln Glu Val Arg Val Cys
995 1000 1005

Pro Gly Arg Gly Tyr Ile Leu Arg Val Thr Ala Tyr Lys Glu Gly Tyr
1010 1015 1020

Gly Glu Gly Cys Val Thr Ile His Glu Ile Glu Asn Asn Thr Asp Glu
1025 1030 1035 1040

Leu Lys Phe Asn Asn Cys Val Glu Glu Glu Val Tyr Pro Asn Asn Thr
1045 1050 1055

Val Thr Cys Ile Asn Tyr Thr Ala Thr Gln Glu Glu Tyr Glu Gly Thr
1060 1065 1070

Tyr Thr Ser Arg Asn Arg Gly Tyr Asp Glu Ala Tyr Gly Asn Asn Pro
1075 1080 1085

Ser Val Pro Ala Asp Tyr Ala Ser Val Tyr Glu Glu Lys Ser Tyr Thr
1090 1095 1100

Asp Arg Arg Arg Glu Asn Pro Cys Glu Ser Asn Arg Gly Tyr Gly Asp
1105 1110 1115 1120

Tyr Thr Pro Leu Pro Ala Gly Tyr Val Thr Lys Glu Leu Glu Tyr Phe

-continued 1125 1130 1135

Pro Glu Thr Asp Lys Val Trp Ile Glu Ile Gly Glu Thr Glu Gly Thr
1140 1145 1150

Phe Ile Val Asp Ser Val Glu Leu Leu Leu Met Glu Glu
1155 1160 1165

( 2 ) INFORMATION FOR SEQ ID NO:5:

( i ) SEQUENCE CHARACTERISTICS:
( A ) LENGTH: 3567 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IB2

( x i ) SEQUENCE DESCRIPTION: SEQ ID NO:5:

ATGGAGGAAA ATAATCAAAA TCAATGCATA CCTTACAATT GTTTAAGTAA TCCTGAAGAA 60

GTACTTTTGG ATGGAGAACG GATATCAACT GGTAATTCAT CAATTGATAT TTCTCTGTCA 120

CTTGTTCAGT TTCTGGTATC TAACTTTGTA CCAGGGGGAG GATTTTTAGT TGGATTAATA 180

GATTTTGTAT GGGGAATAGT TGGCCCTTCT CAATGGGATG CATTTCTAGT ACAAATTGAA 240

CAATTAATTA ATGAAAGAAT AGCTGAATTT GCTAGGAATG CTGCTATTGC TAATTTAGAA 300

GGATTAGGAA ACAATTTCAA TATATATGTG GAAGCATTTA AAGAATGGGA AGAAGATCCT 360

AATAATCCAG CAACCAGGAC CAGAGTAATT GATCGCTTTC GTATACTTGA TGGGCTACTT 420

GAAAGGGACA TTCCTTCGTT TCGAATTTCT GGATTTGAAG TACCCCTTTT ATCCGTTTAT 480

GCTCAAGCGG CCAATCTGCA TCTAGCTATA TTAAGAGATT CTGTAATTTT TGGAGAAAGA 540

TGGGGATTGA CAACGATAAA TGTCAATGAA AACTATAATA GACTAATTAG GCATATTGAT 600

GAATATGCTG ATCACTGTGC AAATACGTAT AATCGGGGAT TAAATAATTT ACCGAAATCT 660

ACGTATCAAG ATTGGATAAC ATATAATCGA TTACGGAGAG ACTTAACATT GACTGTATTA 720

GATATCGCCG CTTTCTTTCC AAACTATGAC AATAGGAGAT ATCCAATTCA GCCAGTTGGT 780

CAACTAACAA GGGAAGTTTA TACGGACCCA TTAATTAATT TTAATCCACA GTTACAGTCT 840

GTAGCTCAAT TACCTACTTT TAACGTTATG GAGAGCAGCG CAATTAGAAA TCCTCATTTA 900

TTTGATATAT TGAATAATCT TACAATCTTT ACGGATTGGT TTAGTGTTGG ACGCAATTTT 960

TATTGGGGAG GACATCGAGT AATATCTAGC CTTATAGGAG GTGGTAACAT AACATCTCCT 1020

ATATATGGAA GAGAGGCGAA CCAGGAGCCT CCAAGATCCT TTACTTTTAA TGGACCGGTA 1080

TTTAGGACTT TATCAAATCC TACTTTACGA TTATTACAGC AACCTTGGCC AGCGCCACCA 1140

TTTAATTTAC GTGGTGTTGA AGGAGTAGAA TTTTCTACAC CTACAAATAG CTTTACGTAT 1200

CGAGGAAGAG GTCAGGTTGA TTCTTTAACT GAATTACCGC CTGAGGATAA TAGTGTGCCA 1260

CCTCGCGAAG GATATAGTCA TCGTTTATGT CATGCAACTT TTGTTCAAAG ATCTGGAACA 1320

CCTTTTTTAA CAACTGGTGT AGTATTTTCT TGGACGCATC GTAGTGCAAC TCTTACAAAT 1380

-continued

ACAATTGATC CAGAGAGAAT TAATCAAATA CCTTTAGTGA AAGGATTTAG AGTTTGGGGG 1440

GGCACCTCTG TCATTACAGG ACCAGGATTT ACAGGAGGGG ATATCCTTCG AAGAAATACC 1500

TTTGGTGATT TTGTATCTCT ACAAGTCAAT ATTAATTCAC CAATTACCCA AAGATACCGT 1560

TTAAGATTTC GTTACGCTTC CAGTAGGGAT GCACGAGTTA TAGTATTAAC AGGAGCGGCA 1620

TCCACAGGAG TGGGAGGCCA AGTTAGTGTA AATATGCCTC TTCAGAAAAC TATGGAAATA 1680

GGGGAGAACT TAACATCTAG AACATTTAGA TATACCGATT TTAGTAATCC TTTTTCATTT 1740

AGAGCTAATC CAGATATAAT TGGGATAAGT GAACAACCTC TATTTGGTGC AGGTTCTATT 1800

AGTAGCGGTG AACTTTATAT AGATAAAATT GAAATTATTC TAGCAGATGC AACATTTGAA 1860

GCAGAATCTG ATTTAGAAAG AGCACAAAAG GCGGTGAATG CCCTGTTTAC TTCTTCCAAT 1920

CAAATCGGGT TAAAAACCGA TGTGACGGAT TATCATATTG ATCAAGTATC CAATTTAGTG 1980

GATTGTTTAT CAGATGAATT TTGTCTGGAT GAAAAGCGAG AATTGTCCGA GAAAGTCAAA 2040

CATGCGAAGC GACTCAGTGA TGAGCGGAAT TTACTTCAAG ATCCAAACTT CAGAGGGATC 2100

AATAGACAAC CAGACCGTGG CTGGAGAGGA AGTACAGATA TTACCATCCA AGGAGGAGAT 2160

GACGTATTCA AAGAGAATTA CGTCACACTA CCGGGTACCG TTGATGAGTG CTATCCAACG 2220

TATTTATATC AGAAAATAGA TGAGTCGAAA TTAAAAGCTT ATACCCGTTA TGAATTAAGA 2280

GGGTATATCG AAGATAGTCA AGACTTAGAA ATCTATTTGA TCCGTTACAA TGCAAAACAC 2340

GAAATAGTAA ATGTGCCAGG CACGGGTTCC TTATGGCCGC TTTCAGCCCA AAGTCCAATC 2400

GGAAAGTGTG GAGAACCGAA TCGATGCGCG CCACACCTTG AATGGAATCC TGATCTAGAT 2460

TGTTCCTGCA GAGACGGGGA AAAATGTGCA CATCATTCCC ATCATTTCAC CTTGGATATT 2520

GATGTTGGAT GTACAGACTT AAATGAGGAC TTAGGTCTAT GGGTGATATT CAAGATTAAG 2580

ACGCAAGATA ACCATGCAAG ACTAGGGAAT CTAGAGTTTC TCGAAGAGAA ACCATTATTA 2640

GGGGAAGCAC TAGCTCGTGT GAAAAGAGCG GAGAAGAAGT GGAGAGACAA ACGAGAGAAA 2700

CTGCAGTTGG AAACAAATAT TGTTTATAAA GAGGCAAAAG AATCTGTAGA TGCTTTATTT 2760

GTAAACTCTC AATATGATAG ATTACAAGTG AATACGAACA TCGCAATGAT TCATGCGGCA 2820

GATAAACGCG TTCATAGAAT CCGGGAAGCG TATCTGCCAG AGTTGTCTGT GATTCCAGGT 2880

GTCAATGCGG CCATTTTCGA AGAATTAGAG GGACGTATTT TTACAGCGTA TTCCTTATAT 2940

GATGCGAGAA ATGTCATTAA AAATGGCGAT TTCAATAATG GCTTATTATG CTGGAACGTG 3000

AAAGGTCATG TAGATGTAGA AGAGCAAAAC AACCACCGTT CGGTCCTTGT TATCCCAGAA 3060

TGGGAGGCAG AAGTGTCACA AGAGGTTCGT GTCTGTCCAG GTCGTGGCTA TATCCTTCGT 3120

GTCACAGCAT ATAAAGAGGG ATATGGAGAG GGCTGCGTAA CGATCCATGA GATCGAAGAC 3180

AATACAGACG AACTGAAATT CAGCAACTGT GTAGAAGAGG AAGTATATCC AAACAACACA 3240

GTAACGTGTA ATAATTATAC TGGGACTCAA GAAGAATATG AGGGTACGTA CACTTCTCGT 3300

AATCAAGGAT ATGACGAAGC CTATGGTAAT AACCCTTCCG TACCAGCTGA TTACGCTTCA 3360

GTCTATGAAG AAAAATCGTA TACAGATGGA CGAAGAGAGA ATCCTTGTGA ATCTAACAGA 3420

GGCTATGGGG ATTACACACC ACTACCGGCT GGTTATGTAA CAAAGGATTT AGAGTACTTC 3480

CCAGAGACCG ATAAGGTATG GATTGAGATC GGAGAAACAG AAGGAACATT CATCGTGGAT 3540

AGCGTGGAAT TACTCCTTAT GGAGGAA 3567

( 2 ) INFORMATION FOR SEQ ID NO:6:

( i ) SEQUENCE CHARACTERISTICS:

( A ) LENGTH: 1189 amino acids ( B ) TYPE: amino acid (C) STRANDEDNESS: single
(D) TOPOLOGY: linear (ii) MOLECULE TYPE: protein (iii) HYPOTHETICAL: YES (iv) ANTI-SENSE: NO (vi) ORIGINAL SOURCE:
(A) ORGANISM: BACILLUS THURINGIENSIS
(B) STRAIN: AIZAWAI
(C) INDIVIDUAL ISOLATE: PS81I (vii) IMMEDIATE SOURCE:
(A) LIBRARY: LAMBDAGEM (TM) - 11 LIBRARY OF AUGUST SICK
(B) CLONE: 81IB2

(xi) SEQUENCE DESCRIPTION: SEQ ID NO:6:

| | | | | | | | | | | | | | | | |
|---|---|---|---|---|---|---|---|---|---|---|---|---|---|---|---|
| Met | Glu | Glu | Asn | Asn | Gln | Asn | Gln | Cys | Ile | Pro | Tyr | Asn | Cys | Leu | Ser |
| 1 | | | | 5 | | | | | 10 | | | | | 15 | |
| Asn | Pro | Glu | Glu | Val | Leu | Leu | Asp | Gly | Glu | Arg | Ile | Ser | Thr | Gly | Asn |
| | | | 20 | | | | | 25 | | | | | 30 | | |
| Ser | Ser | Ile | Asp | Ile | Ser | Leu | Ser | Leu | Val | Gln | Phe | Leu | Val | Ser | Asn |
| | | 35 | | | | | 40 | | | | | 45 | | | |
| Phe | Val | Pro | Gly | Gly | Gly | Phe | Leu | Val | Gly | Leu | Ile | Asp | Phe | Val | Trp |
| | 50 | | | | | 55 | | | | | 60 | | | | |
| Gly | Ile | Val | Gly | Pro | Ser | Gln | Trp | Asp | Ala | Phe | Leu | Val | Gln | Ile | Glu |
| 65 | | | | | 70 | | | | | 75 | | | | | 80 |
| Gln | Leu | Ile | Asn | Glu | Arg | Ile | Ala | Glu | Phe | Ala | Arg | Asn | Ala | Ala | Ile |
| | | | | 85 | | | | | 90 | | | | | 95 | |
| Ala | Asn | Leu | Glu | Gly | Leu | Gly | Asn | Asn | Phe | Asn | Ile | Tyr | Val | Glu | Ala |
| | | | 100 | | | | | 105 | | | | | 110 | | |
| Phe | Lys | Glu | Trp | Glu | Glu | Asp | Pro | Asn | Asn | Pro | Ala | Thr | Arg | Thr | Arg |
| | | 115 | | | | | 120 | | | | | 125 | | | |
| Val | Ile | Asp | Arg | Phe | Arg | Ile | Leu | Asp | Gly | Leu | Leu | Glu | Arg | Asp | Ile |
| | 130 | | | | | 135 | | | | | 140 | | | | |
| Pro | Ser | Phe | Arg | Ile | Ser | Gly | Phe | Glu | Val | Pro | Leu | Leu | Ser | Val | Tyr |
| 145 | | | | | 150 | | | | | 155 | | | | | 160 |
| Ala | Gln | Ala | Ala | Asn | Leu | His | Leu | Ala | Ile | Leu | Arg | Asp | Ser | Val | Ile |
| | | | | 165 | | | | | 170 | | | | | 175 | |
| Phe | Gly | Glu | Arg | Trp | Gly | Leu | Thr | Thr | Ile | Asn | Val | Asn | Glu | Asn | Tyr |
| | | | 180 | | | | | 185 | | | | | 190 | | |
| Asn | Arg | Leu | Ile | Arg | His | Ile | Asp | Glu | Tyr | Ala | Asp | His | Cys | Ala | Asn |
| | | 195 | | | | | 200 | | | | | 205 | | | |
| Thr | Tyr | Asn | Arg | Gly | Leu | Asn | Asn | Leu | Pro | Lys | Ser | Thr | Tyr | Gln | Asp |
| | 210 | | | | | 215 | | | | | 220 | | | | |
| Trp | Ile | Thr | Tyr | Asn | Arg | Leu | Arg | Arg | Asp | Leu | Thr | Leu | Thr | Val | Leu |
| 225 | | | | | 230 | | | | | 235 | | | | | 240 |
| Asp | Ile | Ala | Ala | Phe | Phe | Pro | Asn | Tyr | Asp | Asn | Arg | Arg | Tyr | Pro | Ile |
| | | | | 245 | | | | | 250 | | | | | 255 | |
| Gln | Pro | Val | Gly | Gln | Leu | Thr | Arg | Glu | Val | Tyr | Thr | Asp | Pro | Leu | Ile |
| | | | 260 | | | | | 265 | | | | | 270 | | |
| Asn | Phe | Asn | Pro | Gln | Leu | Gln | Ser | Val | Ala | Gln | Leu | Pro | Thr | Phe | Asn |
| | | 275 | | | | | 280 | | | | | 285 | | | |
| Val | Met | Glu | Ser | Ser | Ala | Ile | Arg | Asn | Pro | His | Leu | Phe | Asp | Ile | Leu |
| | 290 | | | | | 295 | | | | | 300 | | | | |
| Asn | Asn | Leu | Thr | Ile | Phe | Thr | Asp | Trp | Phe | Ser | Val | Gly | Arg | Asn | Phe |
| 305 | | | | | 310 | | | | | 315 | | | | | 320 |

-continued

| | | | | | | | | | | | | | | | |
|---|---|---|---|---|---|---|---|---|---|---|---|---|---|---|---|
| Tyr | Trp | Gly | Gly | His | Arg | Val | Ile | Ser | Ser | Leu | Ile | Gly | Gly | Gly | Asn |
| | | | | 325 | | | | | 330 | | | | | 335 | |
| Ile | Thr | Ser | Pro | Ile | Tyr | Gly | Arg | Glu | Ala | Asn | Gln | Glu | Pro | Pro | Arg |
| | | | 340 | | | | | 345 | | | | | 350 | | |
| Ser | Phe | Thr | Phe | Asn | Gly | Pro | Val | Phe | Arg | Thr | Leu | Ser | Asn | Pro | Thr |
| | | 355 | | | | | 360 | | | | | 365 | | | |
| Leu | Arg | Leu | Leu | Gln | Gln | Pro | Trp | Pro | Ala | Pro | Pro | Phe | Asn | Leu | Arg |
| | 370 | | | | | 375 | | | | | 380 | | | | |
| Gly | Val | Glu | Gly | Val | Glu | Phe | Ser | Thr | Pro | Thr | Asn | Ser | Phe | Thr | Tyr |
| 385 | | | | | 390 | | | | | 395 | | | | | 400 |
| Arg | Gly | Arg | Gly | Gln | Val | Asp | Ser | Leu | Thr | Glu | Leu | Pro | Pro | Glu | Asp |
| | | | | 405 | | | | | 410 | | | | | 415 | |
| Asn | Ser | Val | Pro | Pro | Arg | Glu | Gly | Tyr | Ser | His | Arg | Leu | Cys | His | Ala |
| | | | 420 | | | | | 425 | | | | | 430 | | |
| Thr | Phe | Val | Gln | Arg | Ser | Gly | Thr | Pro | Phe | Leu | Thr | Thr | Gly | Val | Val |
| | | 435 | | | | | 440 | | | | | 445 | | | |
| Phe | Ser | Trp | Thr | His | Arg | Ser | Ala | Thr | Leu | Thr | Asn | Thr | Ile | Asp | Pro |
| | 450 | | | | | 455 | | | | | 460 | | | | |
| Glu | Arg | Ile | Asn | Gln | Ile | Pro | Leu | Val | Lys | Gly | Phe | Arg | Val | Trp | Gly |
| 465 | | | | | 470 | | | | | 475 | | | | | 480 |
| Gly | Thr | Ser | Val | Ile | Thr | Gly | Pro | Gly | Phe | Thr | Gly | Gly | Asp | Ile | Leu |
| | | | | 485 | | | | | 490 | | | | | 495 | |
| Arg | Arg | Asn | Thr | Phe | Gly | Asp | Phe | Val | Ser | Leu | Gln | Val | Asn | Ile | Asn |
| | | | 500 | | | | | 505 | | | | | 510 | | |
| Ser | Pro | Ile | Thr | Gln | Arg | Tyr | Arg | Leu | Arg | Phe | Arg | Tyr | Ala | Ser | Ser |
| | | 515 | | | | | 520 | | | | | 525 | | | |
| Arg | Asp | Ala | Arg | Val | Ile | Val | Leu | Thr | Gly | Ala | Ala | Ser | Thr | Gly | Val |
| | 530 | | | | | 535 | | | | | 540 | | | | |
| Gly | Gly | Gln | Val | Ser | Val | Asn | Met | Pro | Leu | Gln | Lys | Thr | Met | Glu | Ile |
| 545 | | | | | 550 | | | | | 555 | | | | | 560 |
| Gly | Glu | Asn | Leu | Thr | Ser | Arg | Thr | Phe | Arg | Tyr | Thr | Asp | Phe | Ser | Asn |
| | | | | 565 | | | | | 570 | | | | | 575 | |
| Pro | Phe | Ser | Phe | Arg | Ala | Asn | Pro | Asp | Ile | Ile | Gly | Ile | Ser | Glu | Gln |
| | | | 580 | | | | | 585 | | | | | 590 | | |
| Pro | Leu | Phe | Gly | Ala | Gly | Ser | Ile | Ser | Ser | Gly | Glu | Leu | Tyr | Ile | Asp |
| | | 595 | | | | | 600 | | | | | 605 | | | |
| Lys | Ile | Glu | Ile | Ile | Leu | Ala | Asp | Ala | Thr | Phe | Glu | Ala | Glu | Ser | Asp |
| | 610 | | | | | 615 | | | | | 620 | | | | |
| Leu | Glu | Arg | Ala | Gln | Lys | Ala | Val | Asn | Ala | Leu | Phe | Thr | Ser | Ser | Asn |
| 625 | | | | | 630 | | | | | 635 | | | | | 640 |
| Gln | Ile | Gly | Leu | Lys | Thr | Asp | Val | Thr | Asp | Tyr | His | Ile | Asp | Gln | Val |
| | | | | 645 | | | | | 650 | | | | | 655 | |
| Ser | Asn | Leu | Val | Asp | Cys | Leu | Ser | Asp | Glu | Phe | Cys | Leu | Asp | Glu | Lys |
| | | | 660 | | | | | 665 | | | | | 670 | | |
| Arg | Glu | Leu | Ser | Glu | Lys | Val | Lys | His | Ala | Lys | Arg | Leu | Ser | Asp | Glu |
| | | 675 | | | | | 680 | | | | | 685 | | | |
| Arg | Asn | Leu | Leu | Gln | Asp | Pro | Asn | Phe | Arg | Gly | Ile | Asn | Arg | Gln | Pro |
| | 690 | | | | | 695 | | | | | 700 | | | | |
| Asp | Arg | Gly | Trp | Arg | Gly | Ser | Thr | Asp | Ile | Thr | Ile | Gln | Gly | Gly | Asp |
| 705 | | | | | 710 | | | | | 715 | | | | | 720 |
| Asp | Val | Phe | Lys | Glu | Asn | Tyr | Val | Thr | Leu | Pro | Gly | Thr | Val | Asp | Glu |
| | | | | 725 | | | | | 730 | | | | | 735 | |
| Cys | Tyr | Pro | Thr | Tyr | Leu | Tyr | Gln | Lys | Ile | Asp | Glu | Ser | Lys | Leu | Lys |
| | | | 740 | | | | | 745 | | | | | 750 | | |

-continued

Ala Tyr Thr Arg Tyr Glu Leu Arg Gly Tyr Ile Glu Asp Ser Gln Asp
755 760 765

Leu Glu Ile Tyr Leu Ile Arg Tyr Asn Ala Lys His Glu Ile Val Asn
770 775 780

Val Pro Gly Thr Gly Ser Leu Trp Pro Leu Ser Ala Gln Ser Pro Ile
785 790 795 800

Gly Lys Cys Gly Glu Pro Asn Arg Cys Ala Pro His Leu Glu Trp Asn
805 810 815

Pro Asp Leu Asp Cys Ser Cys Arg Asp Gly Glu Lys Cys Ala His His
820 825 830

Ser His His Phe Thr Leu Asp Ile Asp Val Gly Cys Thr Asp Leu Asn
835 840 845

Glu Asp Leu Gly Leu Trp Val Ile Phe Lys Ile Lys Thr Gln Asp Asn
850 855 860

His Ala Arg Leu Gly Asn Leu Glu Phe Leu Glu Glu Lys Pro Leu Leu
865 870 875 880

Gly Glu Ala Leu Ala Arg Val Lys Arg Ala Glu Lys Lys Trp Arg Asp
885 890 895

Lys Arg Glu Lys Leu Gln Leu Glu Thr Asn Ile Val Tyr Lys Glu Ala
900 905 910

Lys Glu Ser Val Asp Ala Leu Phe Val Asn Ser Gln Tyr Asp Arg Leu
915 920 925

Gln Val Asn Thr Asn Ile Ala Met Ile His Ala Ala Asp Lys Arg Val
930 935 940

His Arg Ile Arg Glu Ala Tyr Leu Pro Glu Leu Ser Val Ile Pro Gly
945 950 955 960

Val Asn Ala Ala Ile Phe Glu Glu Leu Glu Gly Arg Ile Phe Thr Ala
965 970 975

Tyr Ser Leu Tyr Asp Ala Arg Asn Val Ile Lys Asn Gly Asp Phe Asn
980 985 990

Asn Gly Leu Leu Cys Trp Asn Val Lys Gly His Val Asp Val Glu Glu
995 1000 1005

Gln Asn Asn His Arg Ser Val Leu Val Ile Pro Glu Trp Glu Ala Glu
1010 1015 1020

Val Ser Gln Glu Val Arg Val Cys Pro Gly Arg Gly Tyr Ile Leu Arg
1025 1030 1035 1040

Val Thr Ala Tyr Lys Glu Gly Tyr Gly Glu Gly Cys Val Thr Ile His
1045 1050 1055

Glu Ile Glu Asp Asn Thr Asp Glu Leu Lys Phe Ser Asn Cys Val Glu
1060 1065 1070

Glu Glu Val Tyr Pro Asn Asn Thr Val Thr Cys Asn Asn Tyr Thr Gly
1075 1080 1085

Thr Gln Glu Glu Tyr Glu Gly Thr Tyr Thr Ser Arg Asn Gln Gly Tyr
1090 1095 1100

Asp Glu Ala Tyr Gly Asn Asn Pro Ser Val Pro Ala Asp Tyr Ala Ser
1105 1110 1115 1120

Val Tyr Glu Glu Lys Ser Tyr Thr Asp Gly Arg Arg Glu Asn Pro Cys
1125 1130 1135

Glu Ser Asn Arg Gly Tyr Gly Asp Tyr Thr Pro Leu Pro Ala Gly Tyr
1140 1145 1150

Val Thr Lys Asp Leu Glu Tyr Phe Pro Glu Thr Asp Lys Val Trp Ile
1155 1160 1165

Glu Ile Gly Glu Thr Glu Gly Thr Phe Ile Val Asp Ser Val Glu Leu

-continued 1170 1175 1180

Leu Leu Met Glu Glu
1185

( 2 ) INFORMATION FOR SEQ ID NO:7:

( i ) SEQUENCE CHARACTERISTICS:
( A ) LENGTH: 3522 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IA ( x i ) SEQUENCE DESCRIPTION: SEQ ID NO:7:

ATGGAGAATA ATATTCAAAA TCAATGCGTA CCTTACAATT GTTTAAATAA TCCTGAAGTA 60

GAAATATTAA ATGAAGAAAG AAGTACTGGC AGATTACCGT TAGATATATC CTTATCGCTT 120

ACACGTTTCC TTTTGAGTGA ATTTGTTCCA GGTGTGGGAG TTGCGTTTGG ATTATTTGAT 180

TTAATATGGG GTTTTATAAC TCCTTCTGAT TGGAGCTTAT TTCTTTTACA GATTGAACAA 240

TTGATTGAGC AAAGAATAGA AACATTGGAA AGGAACCGGG CAATTACTAC ATTACGAGGG 300

TTAGCAGATA GCTATGAAAT TTATATTGAA GCACTAAGAG AGTGGGAAGC AAATCCTAAT 360

AATGCACAAT TAAGGGAAGA TGTGCGTATT CGATTTGCTA ATACAGACGA CGCTTTAATA 420

ACAGCAATAA ATAATTTTAC ACTTACAAGT TTTGAAATCC CTCTTTTATC GGTCTATGTT 480

CAAGCGGCGA ATTTACATTT ATCACTATTA AGAGACGCTG TATCGTTTGG GCAGGGTTGG 540

GGACTGGATA TAGCTACTGT TAATAATCAT TATAATAGAT TAATAAATCT TATTCATAGA 600

TATACGAAAC ATTGTTTGGA CACATACAAT CAAGGATTAG AAAACTTAAG AGGTACTAAT 660

ACTCGACAAT GGGCAAGATT CAATCAGTTT AGGAGAGATT TAACACTTAC TGTATTAGAT 720

ATCGTTGCTC TTTTTCCGAA CTACGATGTT AGAACATATC CAATTCAAAC GTCATCCCAA 780

TTAACAAGGG AAATTTATAC AAGTTCAGTA ATTGAGGATT CTCCAGTTTC TGCTAATATA 840

CCTAATGGTT TTAATAGGGC GGAATTTGGA GTTAGACCGC CCCATCTTAT GGACTTTATG 900

AATTCTTTGT TTGTAACTGC AGAGACTGTT AGAAGTCAAA CTGTGTGGGG AGGACACTTA 960

GTTAGTTCAC GAAATACGGC TGGTAACCGT ATAAATTTCC CTAGTTACGG GGTCTTCAAT 1020

CCTGGTGGCG CCATTTGGAT TGCAGATGAG GATCCACGTC CTTTTTATCG GACATTATCA 1080

GATCCTGTTT TTGTCCGAGG AGGATTTGGG AATCCTCATT ATGTACTGGG GCTTAGGGGA 1140

GTAGCATTTC AACAAACTGG TACGAACCAC ACCCGAACAT TTAGAAATAG TGGGACCATA 1200

GATTCTCTAG ATGAAATCCC ACCTCAGGAT AATAGTGGGG CACCTTGGAA TGATTATAGT 1260

CATGTATTAA ATCATGTTAC ATTTGTACGA TGGCCAGGTG AGATTTCAGG AAGTGATTCA 1320

TGGAGAGCTC CAATGTTTTC TTGGACGCAC CGTAGTGCAA CCCCTACAAA TACAATTGAT 1380

CCGGAGAGGA TTACTCAAAT ACCATTGGTA AAAGCACATA CACTTCAGTC AGGTACTACT 1440

GTTGTAAGAG GGCCCGGGTT TACGGGAGGA GATATTCTTC GACGAACAAG TGGAGGACCA 1500

-continued

```
TTTGCTTATA CTATTGTTAA TATAAATGGG CAATTACCCC AAAGGTATCG TGCAAGAATA 1560
CGCTATGCCT CTACTACAAA TCTAAGAATT TACGTAACGG TTGCAGGTGA ACGGATTTTT 1620
GCTGGTCAAT TTAACAAAAC AATGGATACC GGTGACCCAT TAACATTCCA ATCTTTTAGT 1680
TACGCAACTA TTAATACAGC TTTTACATTC CCAATGAGCC AGAGTAGTTT CACAGTAGGT 1740
GCTGATACTT TTAGTTCAGG GAATGAAGTT TATATAGACA GATTTGAATT GATTCCAGTT 1800
ACTGCAACAT TTGAAGCAGA ATATGATTTA GAAAGAGCAC AAAAGGCGGT GAATGCGCTG 1860
TTTACTTCTA TAAACCAAAT AGGGATAAAA ACAGATGTGA CGGATTATCA TATTGATCAA 1920
GTATCCAATT TAGTGGATTG TTTATCAGAT GAATTTTGTC TGGATGAAAA GCGAGAATTG 1980
TCCGAGAAAG TCAAACATGC GAAGCGACTC AGTGATGAGC GGAATTTACT TCAAGATCCA 2040
AACTTCAAAG GCATCAATAG GCAACTAGAC CGTGGTTGGA GAGGAAGTAC GGATATTACC 2100
ATCCAAAGAG GAGATGACGT ATTCAAAGAA AATTATGTCA CACTACCAGG TACCTTTGAT 2160
GAGTGCTATC CAACGTATTT ATATCAAAAA ATAGATGAGT CGAAATTAAA ACCCTATACT 2220
CGTTATCAAT TAAGAGGGTA TATCGAGGAT AGTCAAGACT TAGAAATCTA TTTGATCCGC 2280
TATAATGCAA AACACGAAAC AGTAAATGTG CTAGGTACGG GTTCTTTATG GCCGCTTTCA 2340
GTCCAAAGTC CAATCAGAAA GTGTGGAGAA CCGAATCGAT GCGCGCCACA CCTTGAATGG 2400
AATCCTGATC TAGATTGTTC CTGCAGAGAC GGGGAAAAAT GTGCACATCA TTCGCATCAT 2460
TTCTCCTTGG ACATTGATGT TGGATGTACA GACTTAAATG AGGACTTAGA TGTATGGGTG 2520
ATATTCAAGA TTAAGACGCA AGATGGCCAT GCAAGACTAG GAAATCTAGA GTTTCTCGAA 2580
GAGAAACCAT TAGTCGGGGA AGCACTAGCT CGTGTGAAAA GAGCAGAGAA AAAATGGAGA 2640
GATAAACGTG AAAAATTGGA ATTGGAAACA AATATTGTTT ATAAAGAGGC AAAAGAATCT 2700
GTAGATGCTT TATTTGTAAA CTCTCAATAT GATCAATTAC AAGCGGATAC GAATATTGCC 2760
ATGATTCATG CGGCAGATAA ACGTGTTCAT AGAATTCGGG AAGCGTATCT TCCAGAGTTA 2820
TCTGTGATTC CGGGTGTAAA TGTAGACATT TTCGAAGAAT TAAAAGGGCG TATTTTCACT 2880
GCATTCTTCC TATATGATGC GAGAAATGTC ATTAAAAACG GTGATTTCAA TAATGGCTTA 2940
TCATGCTGGA ACGTGAAAGG GCATGTAGAT GTAGAAGAAC AAAACAACCA CCGTTCGGTC 3000
CTTGTTGTTC CGGAATGGGA AGCAGAAGTG TCACAAGAAG TTCGTGTCTG TCCGGGTCGT 3060
GGCTATATCC TTCGTGTCAC AGCGTACAAG GAGGGATATG GAGAAGGTTG CGTAACCATT 3120
CATGAGATCG AGAACAATAC AGACGAACTG AAGTTTAGCA ACTGCGTAGA AGAGGAAGTC 3180
TATCCAAACA ACACGGTAAC GTGTAATGAT TATACTGCAA ATCAAGAAGA ATACGGGGGT 3240
GCGTACACTT CCCGTAATCG TGGATATGAC GAAACTTATG GAAGCAATTC TTCTGTACCA 3300
GCTGATTATG CGTCAGTCTA TGAAGAAAAA TCGTATACAG ATGGACGAAG AGACAATCCT 3360
TGTGAATCTA ACAGAGGATA TGGGGATTAC ACACCACTAC CAGCTGGCTA TGTGACAAAA 3420
GAATTAGAGT ACTTCCCAGA AACCGATAAG GTATGGATTG AGATCGGAGA AACGGAAGGA 3480
ACATTCATCG TGGACAGCGT GGAATTACTC CTTATGGAGG AA 3522
```

( 2 ) INFORMATION FOR SEQ ID NO:8:

( i ) SEQUENCE CHARACTERISTICS:
( A ) LENGTH: 1174 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IA ( x i ) SEQUENCE DESCRIPTION: SEQ ID NO:8:

| | | | | | | | | | | | | | | | |
|---|---|---|---|---|---|---|---|---|---|---|---|---|---|---|---|
| Met | Glu | Asn | Asn | Ile | Gln | Asn | Gln | Cys | Val | Pro | Tyr | Asn | Cys | Leu | Asn |
| 1 | | | | 5 | | | | | 10 | | | | | 15 | |
| Asn | Pro | Glu | Val | Glu | Ile | Leu | Asn | Glu | Glu | Arg | Ser | Thr | Gly | Arg | Leu |
| | | | 20 | | | | | 25 | | | | | 30 | | |
| Pro | Leu | Asp | Ile | Ser | Leu | Ser | Leu | Thr | Arg | Phe | Leu | Leu | Ser | Glu | Phe |
| | | 35 | | | | | 40 | | | | | 45 | | | |
| Val | Pro | Gly | Val | Gly | Val | Ala | Phe | Gly | Leu | Phe | Asp | Leu | Ile | Trp | Gly |
| | 50 | | | | | 55 | | | | | 60 | | | | |
| Phe | Ile | Thr | Pro | Ser | Asp | Trp | Ser | Leu | Phe | Leu | Leu | Gln | Ile | Glu | Gln |
| 65 | | | | | 70 | | | | | 75 | | | | | 80 |
| Leu | Ile | Glu | Gln | Arg | Ile | Glu | Thr | Leu | Glu | Arg | Asn | Arg | Ala | Ile | Thr |
| | | | | 85 | | | | | 90 | | | | | 95 | |
| Thr | Leu | Arg | Gly | Leu | Ala | Asp | Ser | Tyr | Glu | Ile | Tyr | Ile | Glu | Ala | Leu |
| | | | 100 | | | | | 105 | | | | | 110 | | |
| Arg | Glu | Trp | Glu | Ala | Asn | Pro | Asn | Asn | Ala | Gln | Leu | Arg | Glu | Asp | Val |
| | | 115 | | | | | 120 | | | | | 125 | | | |
| Arg | Ile | Arg | Phe | Ala | Asn | Thr | Asp | Asp | Ala | Leu | Ile | Thr | Ala | Ile | Asn |
| | 130 | | | | | 135 | | | | | 140 | | | | |
| Asn | Phe | Thr | Leu | Thr | Ser | Phe | Glu | Ile | Pro | Leu | Leu | Ser | Val | Tyr | Val |
| 145 | | | | | 150 | | | | | 155 | | | | | 160 |
| Gln | Ala | Ala | Asn | Leu | His | Leu | Ser | Leu | Leu | Arg | Asp | Ala | Val | Ser | Phe |
| | | | | 165 | | | | | 170 | | | | | 175 | |
| Gly | Gln | Gly | Trp | Gly | Leu | Asp | Ile | Ala | Thr | Val | Asn | Asn | His | Tyr | Asn |
| | | | 180 | | | | | 185 | | | | | 190 | | |
| Arg | Leu | Ile | Asn | Leu | Ile | His | Arg | Tyr | Thr | Lys | His | Cys | Leu | Asp | Thr |
| | | 195 | | | | | 200 | | | | | 205 | | | |
| Tyr | Asn | Gln | Gly | Leu | Glu | Asn | Leu | Arg | Gly | Thr | Asn | Thr | Arg | Gln | Trp |
| | 210 | | | | | 215 | | | | | 220 | | | | |
| Ala | Arg | Phe | Asn | Gln | Phe | Arg | Arg | Asp | Leu | Thr | Leu | Thr | Val | Leu | Asp |
| 225 | | | | | 230 | | | | | 235 | | | | | 240 |
| Ile | Val | Ala | Leu | Phe | Pro | Asn | Tyr | Asp | Val | Arg | Thr | Tyr | Pro | Ile | Gln |
| | | | | 245 | | | | | 250 | | | | | 255 | |
| Thr | Ser | Ser | Gln | Leu | Thr | Arg | Glu | Ile | Tyr | Thr | Ser | Ser | Val | Ile | Glu |
| | | | 260 | | | | | 265 | | | | | 270 | | |
| Asp | Ser | Pro | Val | Ser | Ala | Asn | Ile | Pro | Asn | Gly | Phe | Asn | Arg | Ala | Glu |
| | | 275 | | | | | 280 | | | | | 285 | | | |
| Phe | Gly | Val | Arg | Pro | Pro | His | Leu | Met | Asp | Phe | Met | Asn | Ser | Leu | Phe |
| | 290 | | | | | 295 | | | | | 300 | | | | |
| Val | Thr | Ala | Glu | Thr | Val | Arg | Ser | Gln | Thr | Val | Trp | Gly | Gly | His | Leu |
| 305 | | | | | 310 | | | | | 315 | | | | | 320 |
| Val | Ser | Ser | Arg | Asn | Thr | Ala | Gly | Asn | Arg | Ile | Asn | Phe | Pro | Ser | Tyr |
| | | | | 325 | | | | | 330 | | | | | 335 | |
| Gly | Val | Phe | Asn | Pro | Gly | Gly | Ala | Ile | Trp | Ile | Ala | Asp | Glu | Asp | Pro |
| | | | 340 | | | | | 345 | | | | | 350 | | |

-continued

| | | | | | | | | | | | | | | | |
|---|---|---|---|---|---|---|---|---|---|---|---|---|---|---|---|
| Arg | Pro | Phe | Tyr | Arg | Thr | Leu | Ser | Asp | Pro | Val | Phe | Val | Arg | Gly | Gly |
| | | 355 | | | | | 360 | | | | | 365 | | | |
| Phe | Gly | Asn | Pro | His | Tyr | Val | Leu | Gly | Leu | Arg | Gly | Val | Ala | Phe | Gln |
| | 370 | | | | | 375 | | | | | 380 | | | | |
| Gln | Thr | Gly | Thr | Asn | His | Thr | Arg | Thr | Phe | Arg | Asn | Ser | Gly | Thr | Ile |
| 385 | | | | | 390 | | | | | 395 | | | | | 400 |
| Asp | Ser | Leu | Asp | Glu | Ile | Pro | Pro | Gln | Asp | Asn | Ser | Gly | Ala | Pro | Trp |
| | | | | 405 | | | | | 410 | | | | | 415 | |
| Asn | Asp | Tyr | Ser | His | Val | Leu | Asn | His | Val | Thr | Phe | Val | Arg | Trp | Pro |
| | | | 420 | | | | | 425 | | | | | 430 | | |
| Gly | Glu | Ile | Ser | Gly | Ser | Asp | Ser | Trp | Arg | Ala | Pro | Met | Phe | Ser | Trp |
| | | 435 | | | | | 440 | | | | | 445 | | | |
| Thr | His | Arg | Ser | Ala | Thr | Pro | Thr | Asn | Thr | Ile | Asp | Pro | Glu | Arg | Ile |
| | 450 | | | | | 455 | | | | | 460 | | | | |
| Thr | Gln | Ile | Pro | Leu | Val | Lys | Ala | His | Thr | Leu | Gln | Ser | Gly | Thr | Thr |
| 465 | | | | | 470 | | | | | 475 | | | | | 480 |
| Val | Val | Arg | Gly | Pro | Gly | Phe | Thr | Gly | Gly | Asp | Ile | Leu | Arg | Arg | Thr |
| | | | | 485 | | | | | 490 | | | | | 495 | |
| Ser | Gly | Gly | Pro | Phe | Ala | Tyr | Thr | Ile | Val | Asn | Ile | Asn | Gly | Gln | Leu |
| | | | 500 | | | | | 505 | | | | | 510 | | |
| Pro | Gln | Arg | Tyr | Arg | Ala | Arg | Ile | Arg | Tyr | Ala | Ser | Thr | Thr | Asn | Leu |
| | | 515 | | | | | 520 | | | | | 525 | | | |
| Arg | Ile | Tyr | Val | Thr | Val | Ala | Gly | Glu | Arg | Ile | Phe | Ala | Gly | Gln | Phe |
| | 530 | | | | | 535 | | | | | 540 | | | | |
| Asn | Lys | Thr | Met | Asp | Thr | Gly | Asp | Pro | Leu | Thr | Phe | Gln | Ser | Phe | Ser |
| 545 | | | | | 550 | | | | | 555 | | | | | 560 |
| Tyr | Ala | Thr | Ile | Asn | Thr | Ala | Phe | Thr | Phe | Pro | Met | Ser | Gln | Ser | Ser |
| | | | | 565 | | | | | 570 | | | | | 575 | |
| Phe | Thr | Val | Gly | Ala | Asp | Thr | Phe | Ser | Ser | Gly | Asn | Glu | Val | Tyr | Ile |
| | | | 580 | | | | | 585 | | | | | 590 | | |
| Asp | Arg | Phe | Glu | Leu | Ile | Pro | Val | Thr | Ala | Thr | Phe | Glu | Ala | Glu | Tyr |
| | | 595 | | | | | 600 | | | | | 605 | | | |
| Asp | Leu | Glu | Arg | Ala | Gln | Lys | Ala | Val | Asn | Ala | Leu | Phe | Thr | Ser | Ile |
| | 610 | | | | | 615 | | | | | 620 | | | | |
| Asn | Gln | Ile | Gly | Ile | Lys | Thr | Asp | Val | Thr | Asp | Tyr | His | Ile | Asp | Gln |
| 625 | | | | | 630 | | | | | 635 | | | | | 640 |
| Val | Ser | Asn | Leu | Val | Asp | Cys | Leu | Ser | Asp | Glu | Phe | Cys | Leu | Asp | Glu |
| | | | | 645 | | | | | 650 | | | | | 655 | |
| Lys | Arg | Glu | Leu | Ser | Glu | Lys | Val | Lys | His | Ala | Lys | Arg | Leu | Ser | Asp |
| | | | 660 | | | | | 665 | | | | | 670 | | |
| Glu | Arg | Asn | Leu | Leu | Gln | Asp | Pro | Asn | Phe | Lys | Gly | Ile | Asn | Arg | Gln |
| | | 675 | | | | | 680 | | | | | 685 | | | |
| Leu | Asp | Arg | Gly | Trp | Arg | Gly | Ser | Thr | Asp | Ile | Thr | Ile | Gln | Arg | Gly |
| | 690 | | | | | 695 | | | | | 700 | | | | |
| Asp | Asp | Val | Phe | Lys | Glu | Asn | Tyr | Val | Thr | Leu | Pro | Gly | Thr | Phe | Asp |
| 705 | | | | | 710 | | | | | 715 | | | | | 720 |
| Glu | Cys | Tyr | Pro | Thr | Tyr | Leu | Tyr | Gln | Lys | Ile | Asp | Glu | Ser | Lys | Leu |
| | | | | 725 | | | | | 730 | | | | | 735 | |
| Lys | Pro | Tyr | Thr | Arg | Tyr | Gln | Leu | Arg | Gly | Tyr | Ile | Glu | Asp | Ser | Gln |
| | | | 740 | | | | | 745 | | | | | 750 | | |
| Asp | Leu | Glu | Ile | Tyr | Leu | Ile | Arg | Tyr | Asn | Ala | Lys | His | Glu | Thr | Val |
| | | 755 | | | | | 760 | | | | | 765 | | | |
| Asn | Val | Leu | Gly | Thr | Gly | Ser | Leu | Trp | Pro | Leu | Ser | Val | Gln | Ser | Pro |

-continued 770 775 780

Ile Arg Lys Cys Gly Glu Pro Asn Arg Cys Ala Pro His Leu Glu Trp
785 790 795 800

Asn Pro Asp Leu Asp Cys Ser Cys Arg Asp Gly Glu Lys Cys Ala His
805 810 815

His Ser His His Phe Ser Leu Asp Ile Asp Val Gly Cys Thr Asp Leu
820 825 830

Asn Glu Asp Leu Asp Val Trp Val Ile Phe Lys Ile Lys Thr Gln Asp
835 840 845

Gly His Ala Arg Leu Gly Asn Leu Glu Phe Leu Glu Glu Lys Pro Leu
850 855 860

Val Gly Glu Ala Leu Ala Arg Val Lys Arg Ala Glu Lys Lys Trp Arg
865 870 875 880

Asp Lys Arg Glu Lys Leu Glu Leu Glu Thr Asn Ile Val Tyr Lys Glu
885 890 895

Ala Lys Glu Ser Val Asp Ala Leu Phe Val Asn Ser Gln Tyr Asp Gln
900 905 910

Leu Gln Ala Asp Thr Asn Ile Ala Met Ile His Ala Ala Asp Lys Arg
915 920 925

Val His Arg Ile Arg Glu Ala Tyr Leu Pro Glu Leu Ser Val Ile Pro
930 935 940

Gly Val Asn Val Asp Ile Phe Glu Glu Leu Lys Gly Arg Ile Phe Thr
945 950 955 960

Ala Phe Phe Leu Tyr Asp Ala Arg Asn Val Ile Lys Asn Gly Asp Phe
965 970 975

Asn Asn Gly Leu Ser Cys Trp Asn Val Lys Gly His Val Asp Val Glu
980 985 990

Glu Gln Asn Asn His Arg Ser Val Leu Val Val Pro Glu Trp Glu Ala
995 1000 1005

Glu Val Ser Gln Glu Val Arg Val Cys Pro Gly Arg Gly Tyr Ile Leu
1010 1015 1020

Arg Val Thr Ala Tyr Lys Glu Gly Tyr Gly Glu Gly Cys Val Thr Ile
1025 1030 1035 1040

His Glu Ile Glu Asn Asn Thr Asp Glu Leu Lys Phe Ser Asn Cys Val
1045 1050 1055

Glu Glu Glu Val Tyr Pro Asn Asn Thr Val Thr Cys Asn Asp Tyr Thr
1060 1065 1070

Ala Asn Gln Glu Glu Tyr Gly Gly Ala Tyr Thr Ser Arg Asn Arg Gly
1075 1080 1085

Tyr Asp Glu Thr Tyr Gly Ser Asn Ser Ser Val Pro Ala Asp Tyr Ala
1090 1095 1100

Ser Val Tyr Glu Glu Lys Ser Tyr Thr Asp Gly Arg Arg Asp Asn Pro
1105 1110 1115 1120

Cys Glu Ser Asn Arg Gly Tyr Gly Asp Tyr Thr Pro Leu Pro Ala Gly
1125 1130 1135

Tyr Val Thr Lys Glu Leu Glu Tyr Phe Pro Glu Thr Asp Lys Val Trp
1140 1145 1150

Ile Glu Ile Gly Glu Thr Glu Gly Thr Phe Ile Val Asp Ser Val Glu
1155 1160 1165

Leu Leu Leu Met Glu Glu
1170

*BACILLUS THURINGIENSIS* ISOLATE ACTIVE AGAINST LEPIDOPTERAN PESTS

CROSS-REFERENCE TO A RELATED APPLICATION

This application is a continuation, of application Ser. No. 08/210,110, filed Mar. 17, 1994, abandoned, which is a continuation, of application Ser. No. 07/865,168, abandoned, filed Apr. 9, 1992, which is a division, of application Ser. No. 07/451,261, filed Dec. 14, 1989, now U.S. Pat. No. 5,188,960, which is a continuation-in-part of Ser. No. 07/371,955, filed Jun. 27, 1989 now U.S. Pat. No. 5,126,133.

BACKGROUND OF THE INVENTION

The most widely used microbial pesticides are derived from the bacterium *Bacillus thuringiensis.* This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. kurstaki HD-1 produces a crystal inclusion consisting of a biotoxin called a delta toxin which is toxic to the larvae of a number of lepidopteran insects. The cloning, sequencing, and expression of this B.t. crystal protein gene in *Escherichia coli* has been described in the published literature (Schnepf, H. E. and Whitely, H. R. [1981]Proc. Natl. Acad. Sci. USA 78:2893–2897; Schnepf et al.). U.S. Pat. No. 4,448,885 and U.S. Pat. No. 4,467,036 both disclose the expression of B.t. crystal protein in *E. coli.*

BRIEF SUMMARY OF THE INVENTION

The subject invention concerns a novel *Bacillus thuringiensis* isolate designated B.t. PS81I which has activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises the novel B.t. isolate denoted B.t. PS81I, mutants thereof, and novel δ-endotoxin genes derived from this B.t. isolate which encode proteins which are active against lepidopteran pests.

BRIEF DESCRIPTION OF THE SEQUENCES

Figure 1:
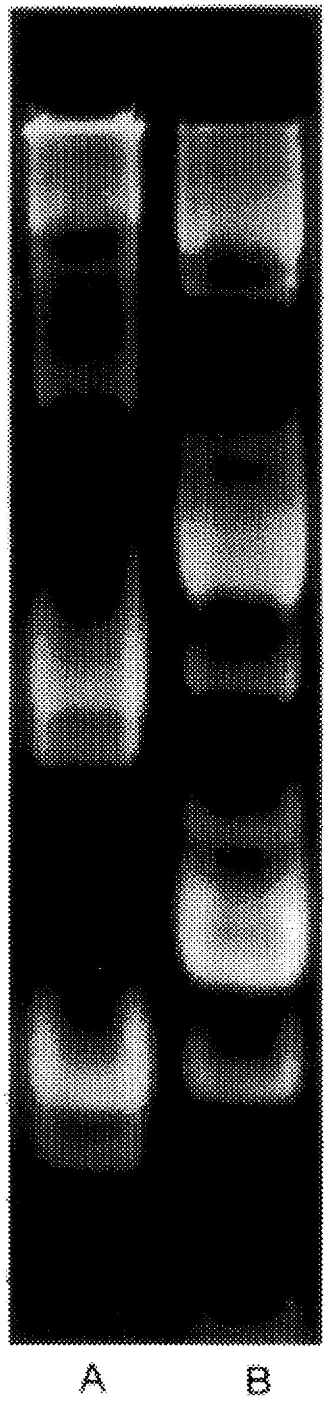
FIG. 1—agarose gel electrophoresis of plasmid preparations from B.t. HD-1 and B.t. PS81I.

SEQ. ID NO. 1 is the nucleotide sequence encoding the novel B.t. toxin gene PS81IA2.

SEQ. ID NO. 2 is the amino acid sequence encoding the novel B.t. toxin gene PS81IA2.

SEQ. ID NO. 3 is the nucleotide sequence encoding the novel B.t. toxin gene PS81IB SEQ. ID NO. 4 is the amino acid sequence encoding the novel B.t. toxin gene PS81IB.

SEQ. ID NO. 5 is the nucleotide sequence encoding the novel B.t. toxin gene PS81IB2.

SEQ. ID NO. 6 is the amino acid sequence encoding the novel B.t. toxin gene PS81IB2.

SEQ. ID NO. 7 is the nucleotide sequence encoding the novel B.t. toxin gene PS81IA.

SEQ. ID NO. 8 is the amino acid sequence encoding the novel B.t. toxin gene PS81IA.

DETAILED DISCLOSURE OF THE INVENTION

The novel toxin genes of the subject invention were obtained from a novel lepidopteran-active *B. thuringiensis* (B.t.) isolate designated PS81I.

Characteristics of B.t. PS81I

Colony morphology—Large colony, dull surface, typical B.t.

Vegetative cell morphology—typical B.t.

Flagella serotype—7, aizawai.

Intracellular inclusions—sporulating cells produce a bipyramidal crystal.

Plasmid preparations—agarose gel electrophoresis of plasmid preparations distinguishing B.t. PS81I from B.t. HD-1. See FIG. 1.

Alkali-soluble proteins—SDS-PAGE analysis shows a protein band at ca. 130,000 daltons.

Unique toxins—four unique toxins have been identified in B.t. PS81I.

Activity—B.t. PS81I kills all Lepidoptera tested.

Bioassay procedures:

B.t. PS81I spores and crystals were tested against: Beet Armyworm, *Spodoptera exigua;* Diamondback Moth, *Plutella xylostella*; Western Spruce Budworm, *Choristoneura occidentalis.*

LC50 values were as follows:

Beet Armyworm—2.53 ppm

Diamondback Moth—0.16 ppm

Western Spruce Budworm—3.2 ppm

Bioassay procedure: dilutions are prepared of a spore and crystal pellet, mixed with USDA Insect Diet (Technical Bulletin 1528, U.S. Department of Agriculture), and poured into small plastic trays. Larvae are placed on the diet mixture and held at 25° C. (late 2nd instar Diamondback Moth larvae, early 2nd instar Beet Armyworm larvae, 4th instar Western Spruce Budworm larvae). Mortality is recorded after six days.

*B. thuringiensis* PS81I, NRRL B-18484, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. B.t. PS81I, and mutants thereof, can be used to control lepidopteran pests.

A subculture of B.t. PS81I and the *E. coli* hosts harboring the toxin genes of the invention, were deposited in the permanent collection of the Northern Research Laboratory, U.S. Department of Agriculture, Peoria, Ill., USA. The accession numbers and deposit dates are as follows:

| Subculture | Accession Number | Deposit Date |
|---|---|---|
| *B.t.* PS81I | NRRL B-18484 | April 19, 1989 |
| *E. coli* (NM522)(pMYC392) | NRRL B-18498 | May 17, 1989 |
| *E. coli* (NM522)(pMYC393) | NRRL B-18499 | May 17, 1989 |

-continued

| Subculture | Accession Number | Deposit Date |
|---|---|---|
| *E. coli* (NM522)(pMYC394) | NRRL B-18500 | May 17, 1989 |
| *E. coli* (NM522)(pMYC1603) | NRRL B-18517 | June 30, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus, and Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/rag. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81I can be made by procedures well known in the art. For example, an asporogenous mutant can be obtained through ethylmethane sulfonate (EMS) mutagenesis of PS81I. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS81I

A subculture of B.t. PS81I, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30 ° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes From Isolate PS81I and Transformation into *Escherichia coli*

Total cellular DNA was prepared from B.t. cells grown to a low optical density ($OD_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81I and B.t.k. HD-1 was digested with EcoRI and separated by electrophoresis on a 0.8% (w/v) Agarose-TAE (50 mM Tris-Cl, 20 mM NaOAc, 2.5 mM EDTA, pH=8.0) buffered gel. A Southern blot of the gel was hybridized with a [$^{32}$P] radiolabeled probe against the 3.2 Kb NsiI to NsiI fragment of the toxin gene contained in plasmid pM3,130-7 of NRRL B-18332 and the 2.4 Kb NsiI to KpnI fragment of the "4.5 Kb class" toxin gene (Kronstad and Whitely [1986] Gene USA 43:29–40). These two fragments were combined and used as the probe. Results show that hybridizing fragments of PS81I are distinct from those of HD-1. Specifically, in the 1.5 Kb to 2.5 Kb size range, 2.3 Kb, 1.95 Kb, and 1.6 Kb hybridizing bands were detected in PS81I instead of the single 1.9 Kb hybridizing band in HD-1.

The following description outlines the steps taken in cloning two of the three EcoRI fragments described above. Two hundred micrograms of PS81I total cellular DNA was digested with EcoRI and separated by electrophoresis on a preparative 0.8% (w/v) Agarose-TAE gel. The 1.5 Kb to 2.3 Kb region of the gel was cut out and the DNA from it was electroeluted and concentrated using an ELUTIP™-d (Schleicher and Schuell, Keene, N.H.) ion exchange column according to the manufacturer's specification. The isolated EcoRI fragments were ligated to LAMBDA ZAP™ EcoRI arms (Stratagene Cloning Systems, La Jolla, Calif.) and packaged using Gigapak GOLD™ (Stratagene) extracts. The packaged recombinant phage were plated with *E. coli* strain BB4 (Stratagene) to give high plaque density. The plaques were screened by standard nucleic acid hybridization procedures with radiolabeled probe. The plaques that hybridized were purified and re-screened at a lower plaque density. The resulting purified phage were grown with R408 M13 helper phage (Stratagene) and the recombinant Blue-Script ™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by a standard rapid plasmid purification procedure to identify the desired plasmids. The plasmids, designated pM2,31-4 and pM2,31-1, contain approximately 1.95 Kb and 1.6 Kb EcoRI inserts, respectively. The DNA sequence of both inserts was determined using Stratagene's T7 and T3 oligonucleotide primers plus a set of existing internal B.t. endotoxin gene oligonucleotide primers. About 500 bp of the insert in pM2,31-4 was sequenced. In the same manner, approximately 1.0 Kb of the insert in pM2,31-1 was sequenced. Data analysis comparing the two sequences to other cloned and sequenced B.t. endotoxin genes showed that two distinct, unique partial toxin gene sequences had been found. Synthetic oligonucleotides were constructed to regions in both sequences that had minimum homology to other characterized B.t. endotoxin genes. The 42-mer oligonucleotide constructed to the sequence of the insert in pM2,31-4was GGATACCGGTGACCCATTAACATTCCAATCTTTTAGTTACGC; it was used to isolate a toxin gene sequence called 81IA. The 40-mer oligonucleotide constructed to the sequence of the insert in pM2,31-1 was GAAGTTTATGGCCTCTTTCTGTAGAAAATCAAATTGGACC; it was used to isolate a toxin gene sequence called 81IB.

In order to clone both complete toxin genes, a Sau3A partial library was constructed. PS81I total cellular DNA partially digested with Sau3A and size fractionated by electrophoresis into a mixture of 9-23 Kb fragments on a 0.6% agarose-TAE gel, and purified as described previously, was ligated into LambdaGEM-11™ (PROMEGA). The packaged phage were plated on P2392 *E. coli* cells (Stratagene) at a high titer and screened using the radiolabeled synthetic oligonucleotides (aforementioned) as nucleic acid hybridization probes. Hybridizing plaques, using each probe, were rescreened at a lower plaque density. Purified plaques that hybridized with either probe were used to infect P2392 *E. coli* cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pUC19 (NEB). The ligation mix was introduced by transformation into DH5(α) competent *E. coli cells* (BRL) and plated on LB agar containing ampicillin, isopropyl-(β)-D-thiogalactoside (IPTG), and 5-bromo-4-chloro-3-indolyl-(β)-D-galactoside (XGAL). White colonies, with prospective insertions in the (β)-galactosidase gene of pUC19, were subjected to standard rapid plasmid purification procedures to isolate the desired plasmids. Plasmid pM3,122-1 contains a 15 Kb Sau3A fragment isolated using the 81IA oligonucleotide probe. Plasmid pM4,59-1 contains an 18 Kb Sau3A fragment isolated using the 81IB oligonucleotide probe.

Plasmid pM3,122-1 was digested with several restriction enzymes and Southern blotted. The blot was probed with the [$^{32}$P] radiolabeled 81IA specific oligonucleotide probe, as well as the labeled oligonucleotide sequencing primers made to known B.t.k. toxin genes. The resulting autoradiogram showed that two toxin genes were present in tandem on this cloned Sau3A fragment. Plasmid pM3,122-1 had a 4.0 Kb NdeI fragment that hybridized with oligonucleotide probes made to known B.t.k. genes. This fragment, however, did not hybridize with the specific oligonucleotides to 81IA or 81IB; a new toxin gene had been discovered and subsequently was called 81IA2. The 4.0 Kb NdeI fragment was isolated and cloned in pUC19, yielding plasmid pMYC392. The 81IA toxin gene was isolated by digesting pM3,122-1 with HindIII, with resulting deletion of most of the 81IA2 toxin gene. The fragment was recircularized to form pMYC1603. The 81IA toxin gene is unique based on its restriction map and its DNA sequence.

Plasmid pM4,59-1 was digested with several restriction enzymes and Southern blotted. The blot was probed with the [$^{32}$P] radiolabeled 81IB specific oligonucleotide probe, as well as with labeled oligonucleotide sequencing primers made to known B.t.k. toxin genes. The plasmid pM4,59-1 was mapped and found to contain only a partial 81IB toxin gene. The full open reading frame (ORF) of a second toxin gene was discovered on the 18 Kb fragment and called 81IB2. The 81IB2 toxin gene was cloned separately from the 81IB toxin gene by digestion of pM4,59-1 with NdeI and SmaI, filling in the NdeI overhang and ligating the linear fragment back together. The resulting plasmid was called pMYC394. The full ORF of the 81IB toxin gene was isolated from another Sau3A fragment, cloned from the lambda library, on a 7.3 Kb HindIII fragment in pBluescript (Stratagene). The resulting plasmid is pMYC393.

The toxin genes were sequenced by the standard Sanger dideoxy chain termination method using oligonucleotide primers made to the "4.5 Kb class" toxin gene and by "walking" with primers made to the sequences of the new toxin genes. Sequence analysis of the four toxin genes has elucidated unique open reading frames and has deduced unique endotoxin proteins (SEQ. ID NO. 1–12). The following table summarizes the size of each ORF in base pairs and the deduced endotoxin molecular weight in daltons.

| TOXIN GENE | ORF (bp) | DEDUCED MW (daltons) | SEQ. ID NO. |
|---|---|---|---|
| 81IA2 | 3537 | 133,367 | 1–2 |
| 81IB | 3495 | 132,480 | 3–4 |
| 81IB2 | 3567 | 134,714 | 5–6 |
| 81IA | 3716 | 133,621 | 7–8 |

Endotoxin proteins have been expressed in Pseudomonas and/or Bacillus from the toxin genes. SDS-PAGE/Western blot analysis, using polyclonal antibodies directed against the "6.6 Kb" class toxin, verified that each gene encodes an immunoreactive protein of approximately 130,000 daltons. The toxin proteins encoded by the genes of the subject invention expressed in either a Bacillus or Pseudomonas host have activity against all lepidopteran insects tested: *Trichoplusia ni, Spodoptera exigua, Plutella xylostella*, and *Choristoneura occidentalis.*

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) Molecular Cloning: A Laboratory Manual, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

The plasmids containing the B.t. toxin genes can be removed from the transformed host microbes by use of standard well-known procedures. For example, the host microbes can be subjected to cleared lysate isopycnic density gradient procedures, and the like, to recover the desired plasmid.

EXAMPLE 3

Insertion of Toxin Genes Into Plants

The novel genes coding for the novel insecticidal toxins, as disclosed herein, can be inserted into plant cells using the Ti plasmid from *Agrobacter tumefaciens.* Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *B. thuringiensis* Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel B.t. toxin genes are shown in SEQ. ID No. 1, 3, 5 and 7. The deduced amino acid sequences are shown in SEQ. ID No. 2, 4, 6 and 8.

It is well known in the art that the am/no acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular am/no acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine

G=guanine

C=cytosine

T=thymine

X=T or C if Y is A or G

X=C if Y is C or T

Y=A, G, C or T if X is C

Y=A or G if X is T

W=C or A if Z is A or G

W=C if Z is C or T

Z=A, G, C or T if W is C

Z=A or G if W is A

QR=TC if S is A, G, C or T; alternatively QR=AG if S is T or C

J=A or G

K=T or C

L=A, T, C or G

M=A, C or T

The above shows that the novel amino acid sequences of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

---

We claim:

1. A purified toxin active against lepidopteran insects comprising the amino acid sequence shown in [SEQ ID NO. 2, SEQ ID NO. 4, SEQ ID NO. 6, and] SEQ ID NO. 8.

2. A method for controlling lepidopteran insects which comprises administering to said insects or to the environment of said insects a host transformed to express a *Bacillus thuringiensis* toxin comprising the amino acid sequence shown in SEQ ID NO. 8.

* * * * *

UNITED STATES PATENT AND TRADEMARK OFFICE
CERTIFICATE OF CORRECTION

PATENT NO. : 5,691,308

DATED : November 25, 1997

INVENTOR(S) : Jewel Payne and August J. Sick

It is certified that error appears in the above-identified patent and that said Letters Patent is hereby corrected as shown below:

Column 7, line 54: "cells/rag." should read --cells/mg.--.

Column 11, line 15: "(SEQ. ID NO. 1-12)." should read --(SEQ. ID NO. 1-8).--.

Column 12, line 38: "am/no" should read --amino--;

line 43: "am/no" should read --amino--; and line 47: "Isoleucine (lle)" should read --Isoleucine (Ile)--.

Column 53, lines 3&4, Claim 1:"in [SEQ ID NO. 2, SEQ ID NO. 4, SEQ ID NO. 6, and] SEQ ID NO. 8." should read --in SEQ ID NO. 8.--

Signed and Sealed this

Thirty-first Day of March, 1998

*Attest:*

BRUCE LEHMAN

*Attesting Officer* *Commissioner of Patents and Trademarks*